(12) United States Patent
English et al.

(10) Patent No.: US 7,880,052 B2
(45) Date of Patent: Feb. 1, 2011

(54) LABIAL PAD

(75) Inventors: Jason M. English, Appleton, WI (US); Richard J. Hantke, Appleton, WI (US); Heather A. Sorebo, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1400 days.

(21) Appl. No.: 10/719,613

(22) Filed: Nov. 21, 2003

(65) Prior Publication Data

US 2005/0113775 A1    May 26, 2005

(51) Int. Cl.
*A61F 13/15* (2006.01)
*A61F 13/20* (2006.01)
(52) U.S. Cl. ............. 604/368; 604/385.01; 604/385.17; 604/367; 604/358
(58) Field of Classification Search .................. 604/354, 604/385.01, 385.17, 386, 387, 368, 358
See application file for complete search history.

(56) References Cited

U.S. PATENT DOCUMENTS

| | | | |
|---|---|---|---|
| 3,726,277 A | | 4/1973 | Hirschman |
| 3,856,013 A | * | 12/1974 | Dulle .......................... 604/369 |
| 3,983,873 A | | 10/1976 | Hirschman |
| 4,175,561 A | | 11/1979 | Hirschman |
| 4,324,246 A | * | 4/1982 | Mullane et al. ............. 604/366 |
| 4,381,782 A | | 5/1983 | Mazurak et al. |
| 4,670,011 A | | 6/1987 | Mesek |
| 4,699,823 A | | 10/1987 | Kellenberger et al. |
| RE32,649 E | | 4/1988 | Brandt et al. |
| 4,773,903 A | | 9/1988 | Weisman et al. |
| 4,798,603 A | | 1/1989 | Meyer et al. |
| 4,950,264 A | | 8/1990 | Osborn, III |
| 5,147,343 A | | 9/1992 | Kellenberger |
| 5,281,207 A | | 1/1994 | Chmielewski et al. |
| 5,484,429 A | | 1/1996 | Vukos et al. |
| 5,536,264 A | | 7/1996 | Hsueh et al. |
| 5,536,555 A | * | 7/1996 | Zelazoski et al. ........... 428/138 |
| 5,569,226 A | | 10/1996 | Cohen et al. |
| 5,601,542 A | | 2/1997 | Melius et al. |

(Continued)

FOREIGN PATENT DOCUMENTS

EP    0 597 498 A1    5/1994

(Continued)

OTHER PUBLICATIONS

International Search Report for PCT/US2004/024251 dated Dec. 23, 2004, 5 pages.

*Primary Examiner*—Tatyana Zalukaeva
*Assistant Examiner*—Susan Su
(74) *Attorney, Agent, or Firm*—Armstrong Teasdale, LLP

(57) ABSTRACT

An absorbent article having an absorbent structure sized and configured for insertion at least partially within the vestibule of a female wearer. The absorbent structure has a saturation capacity as determined by a Saturation Capacity and Retention Capacity Test of at least about 15 grams/gram, a retention capacity as determined by the Saturation Capacity and Retention Capacity Test of at least about 3 grams/gram, and an intake time for a first insult of the absorbent structure as determined by an Intake and Rewet Test of no more than about 30 seconds.

42 Claims, 12 Drawing Sheets

U.S. PATENT DOCUMENTS

| | | |
|---|---|---|
| 5,728,082 A | 3/1998 | Gustafsson et al. |
| 5,836,929 A * | 11/1998 | Bewick-Sonntag et al. .. 604/368 |
| 5,843,059 A | 12/1998 | Niemeyer et al. |
| 5,873,867 A | 2/1999 | Coles et al. |
| 6,270,486 B1 | 8/2001 | Brown et al. |
| 6,635,799 B1 * | 10/2003 | Osborn et al. ................ 604/367 |
| 2003/0120225 A1 | 6/2003 | Everhart et al. |
| 2003/0191442 A1 | 10/2003 | Bewick-Sonntag et al. |

FOREIGN PATENT DOCUMENTS

| | | |
|---|---|---|
| EP | 0 703 764 B1 | 4/1996 |
| EP | 0 989 838 B1 | 4/2000 |
| WO | WO 98/57609 A1 | 12/1998 |
| WO | WO 00/41882 A1 | 7/2000 |

\* cited by examiner

FIG. 12

|  | BW (gsm) | Density (g/cc) | SAM (%) | SAM (Vendor) | SAM (Name) | Structure | Sat Cap (g/g) | Ret Cap (g/g) | 1st Intake (sec) | 2nd Intake (sec) | Rewet (g) |
|---|---|---|---|---|---|---|---|---|---|---|---|
| 1 | 340 | 0.09 | -- | -- | -- | 30/70 Cot/Ray | 16.4 | 1.5 | 15 | 60 | 0.81 |
| 2 | 340 | 0.09 | -- | -- | -- | 50/50 Cot/Ray | 12.4 | 2.2 | 20 | 65 | 0.75 |
| 3 | 340 | 0.09 | -- | -- | -- | 70/30 Cot/Ray | 18.7 | 1.6 | 15 | 48 | 0.76 |
| 4 | 210 | 0.09 | -- | -- | -- | 70/30 Cot/Ray | 15.4 | 2.0 | 23 | 83 | 1.08 |
| 5 | 300 | 0.11 | -- | -- | -- | NB416 pulp | 12.1 | 1.6 | 18 | 126 | 0.69 |
| 6 | 210 | 0.09 | 15 | Stockhausen | F 880 | 70/30 Cot/Ray | 20.0 | 3.9 | 24 | 122 | 0.91 |
| 7 | 300 | 0.14 | 25 | Stockhausen | F 880 | CF416 pulp | 18.8 | 7.1 | 39 | 535 | 0.50 |
| 8 | 300 | 0.11 | 15 | Stockhausen | F 880 | NB416 pulp | 15.2 | 5.6 | 27 | 266 | 0.51 |
| 9 | 300 | 0.13 | 35 | Stockhausen | F 880 | NB416 pulp | 16.6 | 7.6 | 29 | 458 | 0.52 |
| 10 | 300 | 0.10 | 15 | Stockhausen | F 9543 | CF416 pulp | 16.6 | 4.5 | 15 | 79 | 0.63 |
| 11 | 300 | 0.13 | 25 | Stockhausen | F 9543 | NB416 pulp | 16.1 | 6.0 | 40 | 900 | 0.54 |

LABIAL PAD

FIELD OF THE INVENTION

This invention relates generally to absorbent articles used for personal care, and more particularly to absorbent articles such as labial pads which are configured for disposition within the vaginal vestibule of a female wearer for catamenial purposes, incontinence protection or both, and provides enhanced liquid handling performance characteristics.

BACKGROUND OF THE INVENTION

Conventional feminine absorbent articles designed to absorb body fluids, including menses, can generally be grouped into three categories. The first category includes absorbent articles such as sanitary napkins and pantiliners which are worn externally about the pudendal area. Sanitary napkins are generally designed for heavy flow use while pantiliners are thinner than sanitary napkins and are generally designed for light or low menstrual flow. Because sanitary napkins and pantiliners are worn between the wearer's thighs, normal physical movement by the wearer, such as walking, bending, twisting, etc., can cause the article to shift from its original position protecting the vulvar area and can also cause discomfort, such as by rubbing or chafing in the sensitive vulvar area. In addition, such articles have a relatively high degree of wearing awareness, i.e., the article can be apparent when worn with tight-fitting clothing, including slacks, body suits, swim suits, or similarly thin or close-fitting garments. While pantiliners have a smaller (e.g., thinner) profile than sanitary napkins to provide a less obtrusive appearance and more comfortable fit, the thin profile pantiliners are still susceptible to undesired shifting or other movement during normal usage which can result in soiling of the wearer's clothing.

Tampons, another category of feminine absorbent articles, are configured for disposition within the vaginal cavity to intercept and retain menstrual flow. Some tampons may not function correctly to prevent leakage because radial expansion of the tampon within the vaginal cavity may not form a perfect seal with the cavity wall.

Labial pads, also referred to as interlabial pads, represents a third and more recently studied category of feminine absorbent articles. Labial pads are generally configured for disposition between a woman's labia majora and extend at least partially into the vestibule of a female wearer. As such, labial pads are considered to be less obtrusive and can be designed to generally seal against the wearer to prevent liquid against flowing past the labial pad.

There is a need, however, to further develop labial pads having improved liquid intake and rewet performance characteristics as well as improved saturation and retention capacity characteristics. Intake performance refers generally to the ability of the absorbent article to rapidly accept fluid into the absorbent article and away from the wearer. It is meaningful to measure liquid intake performance with repeated insults thereby measuring the time it takes for each insult to be taken into the absorbent article. Rewet performance generally refers to the ability of the absorbent article to inhibit previously taken-in liquid against flowing back out through the article when a compressive load is applied thereto, such as during normal activity including walking, sitting, twisting, bending, etc. The purpose of improving intake performance is to reduce the tendency of the absorbent article to leak or otherwise fail to take in exuded liquid during gushes of liquid. A fast intake time corresponds with low residence time of liquid on the outer surface of the article which in turn reduces the likelihood of leakage. Lower rewet corresponds with reduced surface wetness which can improve wearer comfort and helps promote skin health. However, there is generally considered to be an inverse relationship between the intake performance and the rewet performance of absorbent structures.

SUMMARY OF THE INVENTION

In general, an absorbent article of one embodiment of the present invention generally comprises an absorbent structure sized and configured for insertion at least partially within the vestibule of a female wearer. The absorbent structure has a saturation capacity as determined by a Saturation Capacity and Retention Capacity Test of at least about 15 grams/gram, a retention capacity as determined by the Saturation Capacity and Retention Capacity Test of at least about 3 grams/gram, and an intake time for a first insult of the absorbent structure as determined by an Intake and Rewet Test of no more than about 30 seconds.

In another embodiment, the absorbent article generally comprises an absorbent structure sized and configured for insertion at least partially within the vestibule of a female wearer. The absorbent structure comprises in the range of about 5 weight percent to about 35 weight percent superabsorbent material. The absorbent structure also has a basis weight in the range of about 150 to about 400 grams per square meter and a density in the range of about 0.05 to about 0.13 grams per cubic centimeter. The absorbent structure has a saturation capacity as determined by a Saturation Capacity and Retention Capacity Test of at least about 15 grams/gram and a retention capacity as determined by the Saturation Capacity and Retention Capacity Test of at least about 3 grams/gram.

In yet another embodiment, the absorbent article generally comprises an absorbent structure sized and configured for insertion at least partially within the vestibule of a female wearer. The absorbent structure comprises in the range of about 5 weight percent to about 35 weight percent superabsorbent material. The absorbent structure also has a basis weight in the range of about 150 to about 400 grams per square meter and a density in the range of about 0.05 to about 0.13 grams per cubic centimeter. The absorbent structure has an intake time for a first insult of said absorbent structure as determined by an Intake and Rewet Test of no more than about 30 seconds.

Other features of the invention will be in part apparent and in part pointed out hereinafter.

BRIEF DESCRIPTION OF THE DRAWINGS

FIG. 12 is a table showing comparative test results for different absorbent structures, some of which are made in accordance with the present invention.

DESCRIPTION OF THE PREFERRED EMBODIMENTS

Figure 1A:
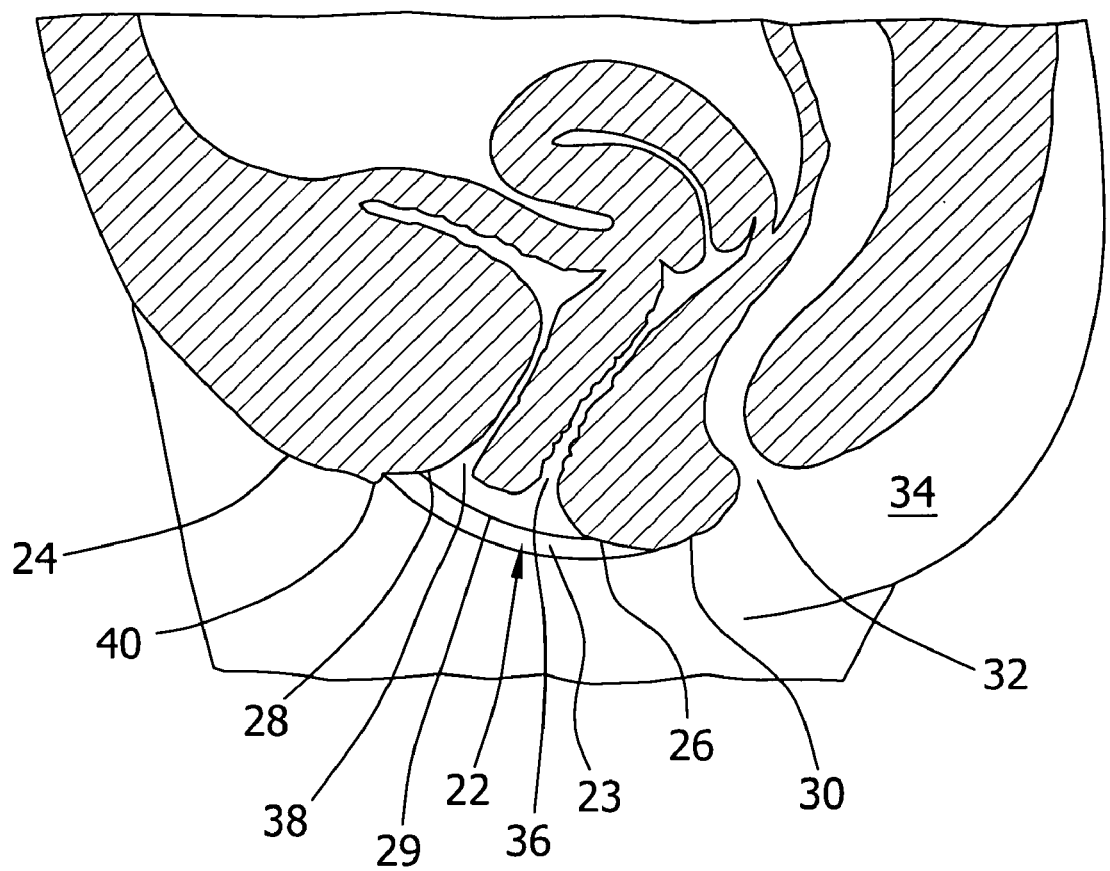
FIG. 1A is a simplified anatomical cross-sectional view of a human female illustrating the environment for an absorbent article of the present invention.
Figure 1B:
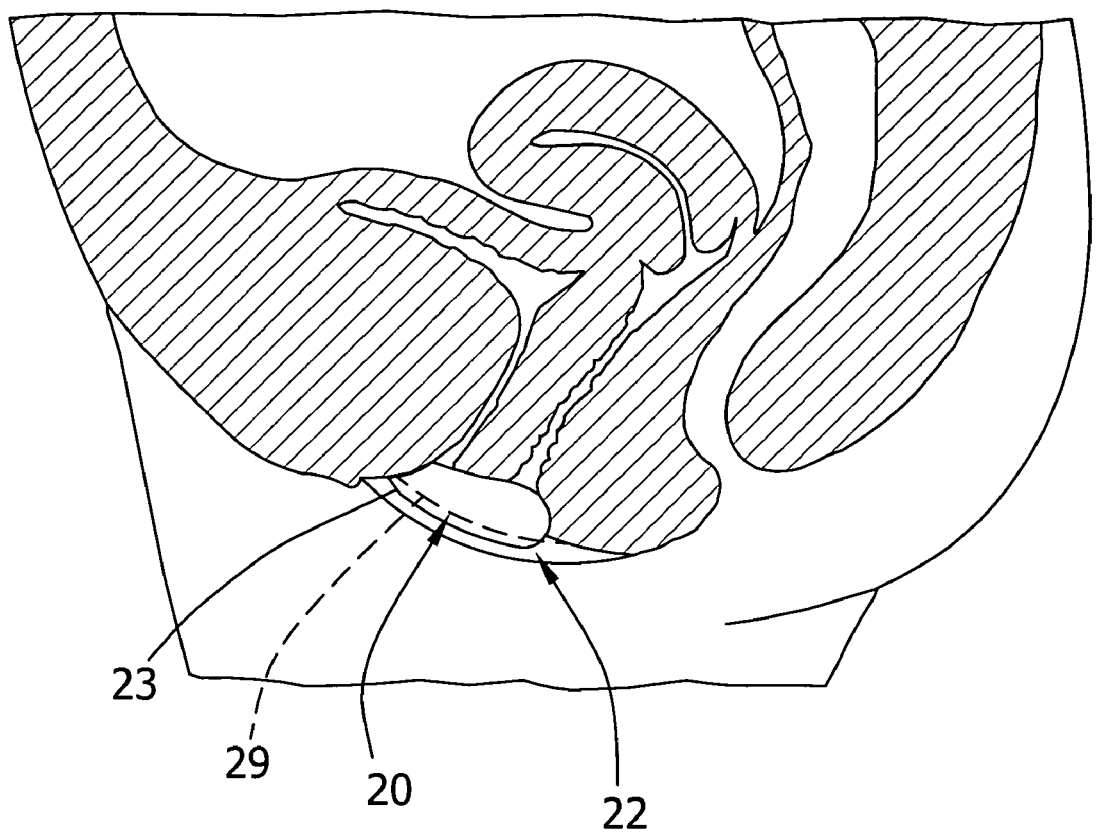
FIG. 1B is a simplified anatomical cross-sectional view of a human female illustrating a placement of an absorbent article in the vestibule of a wearer.

The present invention is directed generally to absorbent articles used for feminine care, and more suitably to labial pads (also commonly referred to as interlabial pads). With reference to FIGS. 1A and 1B, as used herein the term "labial pad" refers to an article, generally indicated at 20, comprising at least some absorbent components and configured for disposition between the labia majora and extending at least partially into the vestibule 22 of a female wearer during use. For purposes of the ensuing description, the vestibule 22 is considered to be the region defined within the labia 23 beginning at about a point lying caudally from the anterior labial commissure 24, extending rearward to the posterior labial commissure 26 and bounded inwardly by the floor 28. One skilled in the art fully understands that there is a wide range of variation among women with respect to the relative size and shape of labia majora and labia minora 29 as the same interrelatedly define the contour of the vestibule 22. For purposes of the present description, however, such differences will not specifically be addressed, it being recognized that in any event the disposition of the absorbent article 20 of the present invention into the vestibule 22 will necessitate placement between the labia majora regardless of any such consideration respecting the labia minora 29.

Lying caudally of the vestibule 22 is the perineum 30, which leads to the anus 32, in the region of the buttocks 34. Within the vestibule 22 itself is located the principal urogenital members which, for reference purposes, are constituted of the vaginal orifice 36, the urethral orifice 38, and the clitoris 40. Given the foregoing simplified review of this anatomical region, and to facilitate the present description, the vestibule 22 will be considered generally to be the region between the clitoris 40 and the posterior labial commissure 26. For a more comprehensive description of this portion of the human female anatomy, however, attention is invited to *Anatomy of the Human Body* by Henry Gray, Thirtieth American Edition (Carmine D. Clemente ed., Lea & Febiger, 1985), at 1571-1581.

During wear, the absorbent article 20 of the present invention is disposed at least partially within the vestibule 22 as indicated in FIG. 1B for at least partially occluding the flow of liquid therefrom. In this regard, the predominant use of the absorbent article 20 is for the absorption of menstrual fluid emitted via the vaginal orifice 36, although the absorbent article of the present invention is equally well adapted to serve as a type of light incontinence device for absorption of urine as occurs upon minor female incontinence.

Figure 2:
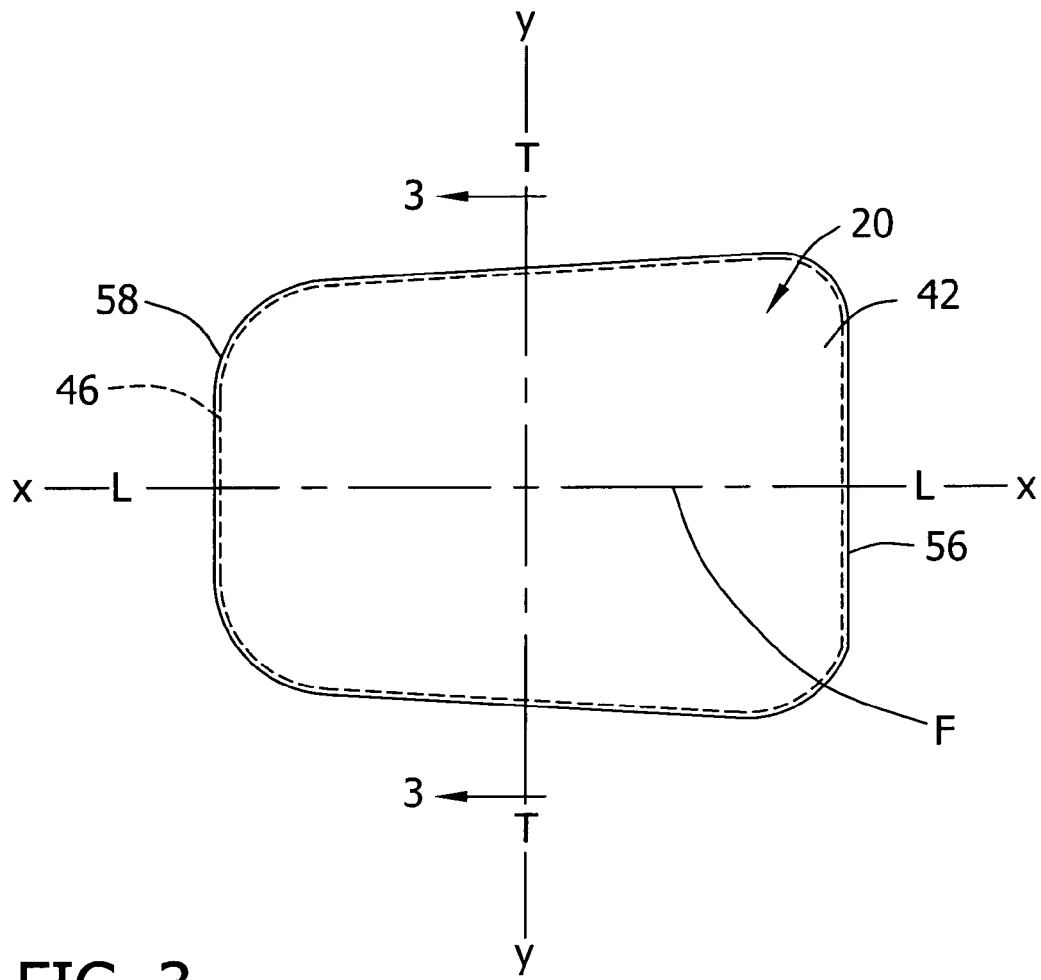
FIG. 2 is a top plan view illustrating an embodiment of a absorbent article of the present invention in the form of a labial pad.
Figure 3:
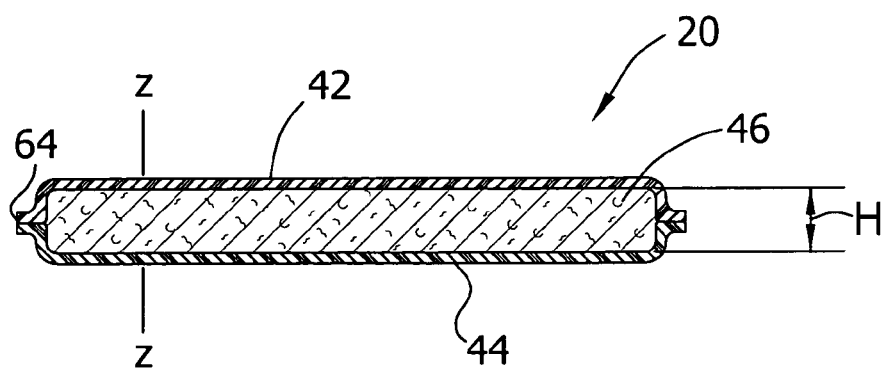
FIG. 3 is cross-section of the absorbent article of FIG. 2 taken in the plane of line 3-3 thereof.
Figure 4:
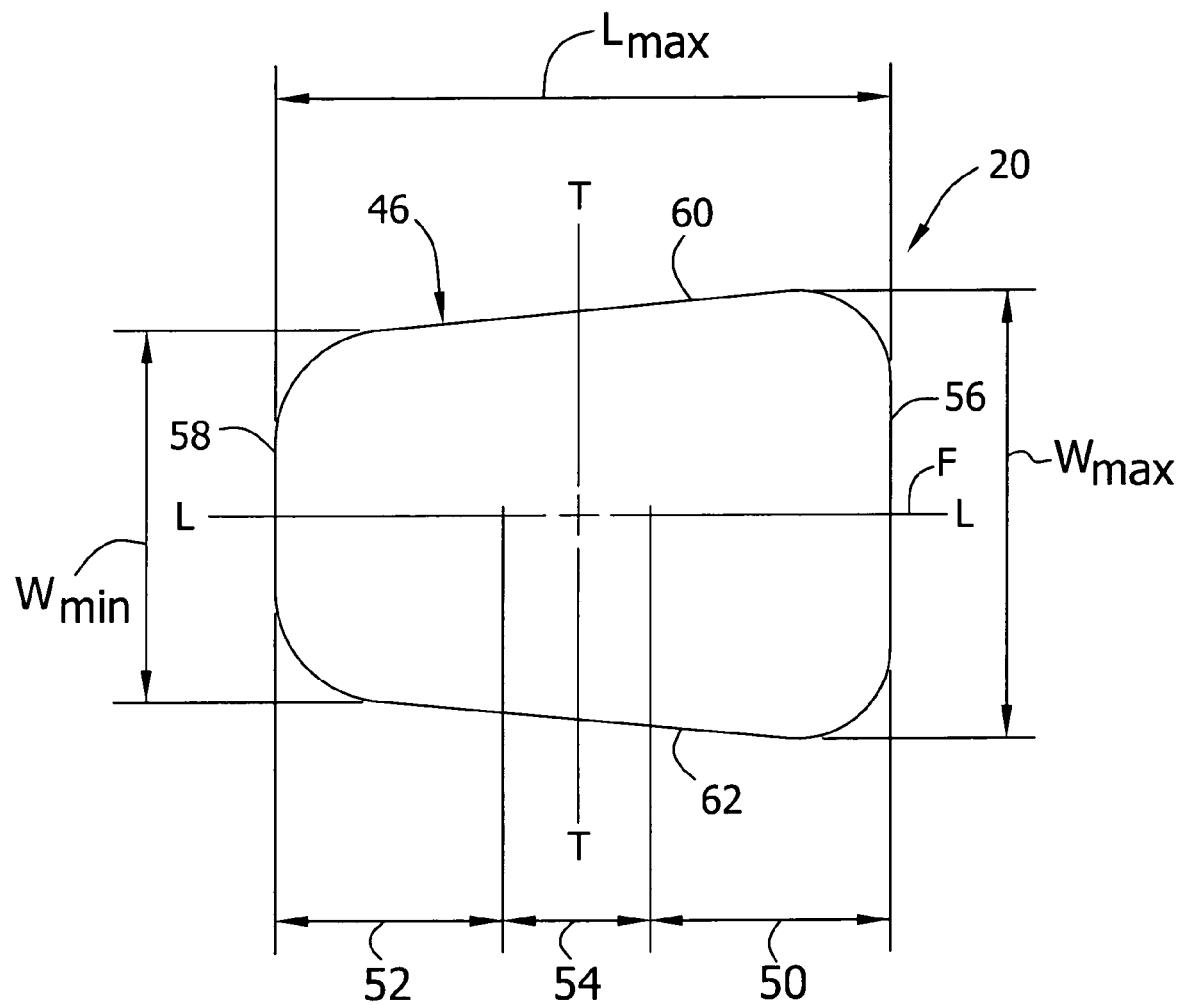
FIG. 4 is a diagrammatic top plan view of the absorbent article of FIG. 2 identifying the geometry of the absorbent article for reference purposes.

The absorbent article 20 according to one embodiment of the present invention is generally illustrated in FIGS. 2-4 as having a principal longitudinal centerline (L-L), which generally runs along the x-axis. As used herein, the term "longitudinal" refers to a line, axis or direction in the plane of the absorbent article 20 that is generally aligned with or parallel to a vertical plane that bisects a standing female wearer into left and right body halves when the absorbent article is in use. The absorbent article 20 has a transverse centerline (T-T) that runs generally along the y-axis normal to the x-axis and in the plane of the absorbent article. The terms "transverse," "lateral" or "y direction" as used herein therefore generally refer to a line, axis or direction that is generally perpendicular to the longitudinal x-axis and in the plane of the absorbent article. A "z direction," generally illustrated in FIG. 3, comprises a line, axis or direction generally perpendicular to the plane defined by the x-axis and y-axis and is parallel to the vertical plane referenced to the female body.

With particular reference to FIG. 3, the absorbent article 20 generally comprises a liquid permeable liner 42 adapted (i.e., positioned relative to the other components of the article) for contiguous relationship with the wearer during use, an outer cover 44 (also sometimes referred to as a baffle) and an absorbent structure disposed between the liner and the outer cover for absorbing liquid taken into the article through the liner. In such an arrangement, the outer surface of the liner 42 broadly defines an inner or body-facing surface of the absorbent article 20 and the outer surface of the outer cover 44 broadly defines an outer surface of the absorbent article.

As illustrated in FIG. 4, the absorbent structure 46 includes longitudinally opposite ends having longitudinally opposite end regions 50, 52 and a central region 54 extending longitudinally between the longitudinal ends of the absorbent structure. The absorbent structure 46 also has laterally opposite side edges 60, 62. The absorbent structure 46, and hence the absorbent article 20, is suitably of a size and shape which allows at least a portion of the absorbent article to be disposed within the vestibule 22 of a female wearer. In addition, the absorbent structure 46 is suitably configured so that the absorbent article at least partially occludes and intercepts the flow of menstrual fluid, urine and/or other bodily exudates from the wearer's vaginal orifice 36 and/or urethral orifice 38. Thus, the geometry of the absorbent article 20, and in particular the absorbent structure 46 therein, is a significant factor affecting the overall size and effectiveness of the absorbent article 20.

In general, the absorbent structure 46 suitably has a maximum width ($W_{max}$), measured along a line laying generally parallel to the transverse centerline (T-T) and running from one side edge 60 to the opposite side edge 62, and a minimum width ($W_{min}$) measured along a line also laying generally parallel to the transverse centerline (T-T) and running from one side edge to the other and being smaller than the maximum width ($W_{max}$). For example, in one embodiment the maximum width ($W_{max}$) of the absorbent structure 46 is disposed generally at one of the end regions 50, while the minimum width ($W_{min}$) of the absorbent structure 46 is disposed at the opposite end region 52. Although, it is understood that the minimum width ($W_{min}$) of the absorbent structure 46 may instead, or may additionally, be disposed at the central region 54. As a further example, the absorbent structure 46 (and hence the absorbent article 20, may have a width ranging between about 40 mm to no greater than about 70 mm; although the approximate width(s) of the absorbent article will vary according to, inter alia, the general design and intended disposition of the absorbent article within the vestibule 22 of a female wearer.

The absorbent structure 46 further has a maximum length ($L_{max}$), measured along a line laying generally parallel to the longitudinal centerline (L-L) and running from one longitudinal end 56 to the other end 58. The absorbent structure 46 may also be configured to have a minimum length ($L_{min}$) measured parallel to the same longitudinal centerline (L-L) which is less than the maximum length ($L_{max}$). As an example, the absorbent structure 46, and hence the absorbent article 20, may have a length in the range of about 60 mm to about 100 mm; although the approximate length(s) of the absorbent article may be varied according to, inter alia, the general design and intended disposition of the absorbent article 20 within the vestibule (22) of a female wearer. The end regions 50, 52 may comprise in the range of about 20% to about 80% of the maximum length ($L_{max}$) of the absorbent structure 46; although the approximate sizes of the end regions will vary according to, inter alia, the general design and intended disposition of the absorbent article 20 within the vestibule 22 of a female wearer.

The absorbent article 20 also has a thickness, or height (H), as illustrated in FIG. 3, measured along a line laying generally parallel to the z-axis. The thickness of the absorbent article 20 is suitably in the range of about 1 mm to about 8 mm, more suitably in the range of about 1 mm to about 5 mm, and still more suitably in the range of about 2 mm to about 3 mm; although the approximate thickness of the absorbent article may be varied according to the general design and intended disposition of the absorbent article within the vestibule 22 of a female wearer.

Figure 6:
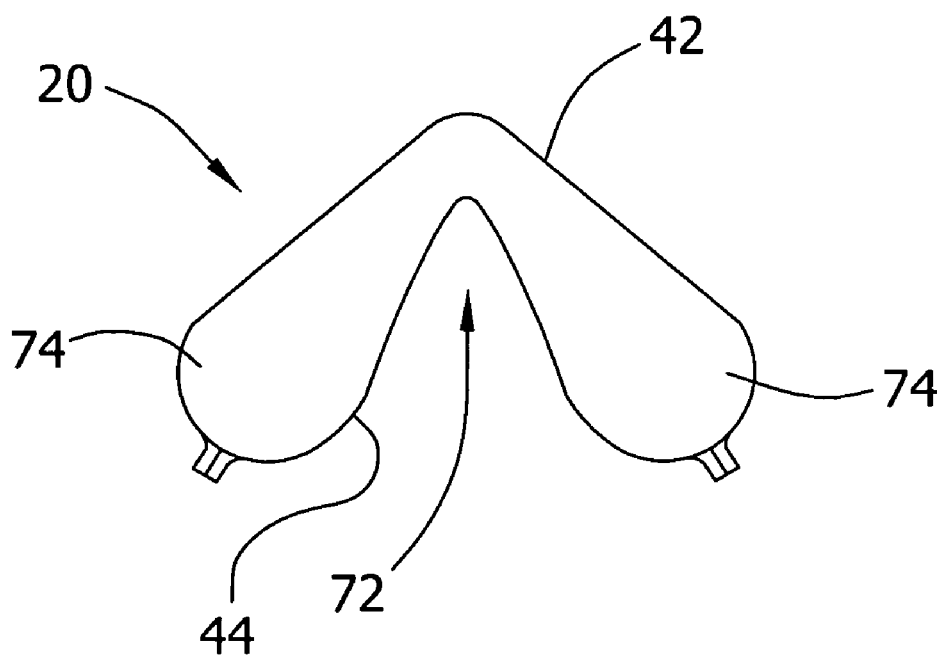
FIG. 6 is a cross-sectional view illustrating the embodiment of FIG. 5 in a folded position.
Figure 7:
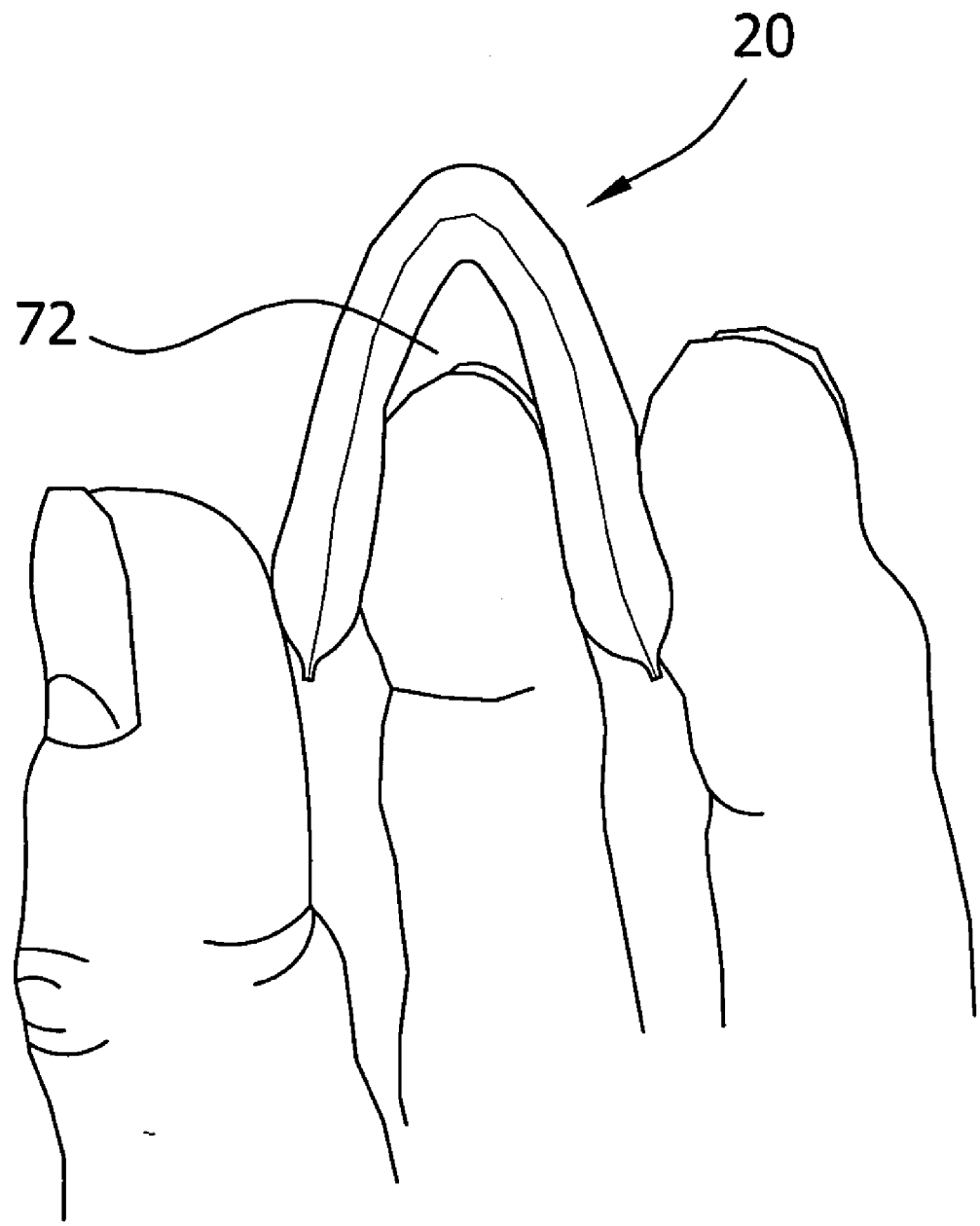
FIG. 7 illustrates greatly enlarged elevational view of an embodiment of an absorbent article folded along a desired axis of flexure and being grasped for disposition in the vestibule by the wearer's fingers.

With particular reference to FIGS. 2, 4 and 7, the absorbent article 20 is suitably foldable for wear by the female wearer. Positioned optionally either on or substantially parallel to the principal longitudinal axis (L-L) of the absorbent article 20, is a desired axis of flexure (F) (FIGS. 2 and 4). The desired line of flexure (F) is generally along the x-axis, but may be off-center slightly therefrom without departing from the scope of this invention. The axis of flexure (F) may result naturally from the dimensions, shape, and/or configuration of the absorbent article 20, or the absorbent structure 46 may be formed with a weakened longitudinal region to create the desired axis of flexure. This desired axis of flexure (F) may also be formed by any of the techniques known to one of skill in the art, including, for example, scoring, pre-folding, slitting, embossing, or the like. One skilled in the art will readily appreciate that a desired axis of flexure (F) may be formed in either the liner 42, the outer cover 44 and/or the absorbent structure 46 or any combination thereof. Typically, the absorbent article 20 is folded along the desired axis of flexure (F), as illustrated generally in FIGS. 6 and 7, prior to disposition within the vestibule (22) of a female wearer.

The geometry of the absorbent article 20 (i.e., one in which the absorbent structure 46 has its maximum width ($W_{max}$) generally at one or both end regions 50, 52) suitably recognizes that a significant number of women do not have vaginal and urethral orifices located at the midpoint of a line extending longitudinally between the clitoris 40 and the posterior labial commissure 26. Although many drawings of the female anatomy illustrate the urethral orifice 38 near the anterior labial commissure 24 and the vaginal orifice 36 near the posterior labial commissure 26 and with the vaginal orifice 36 being significantly larger than the urethral orifice 38, there can be a significant variation in the size and location of both orifices. The longitudinal distance between the urethral orifice 38 and the vaginal orifice 36 can vary significantly, as can the longitudinal distance between the clitoris 40 and the urethral orifice 38 and the longitudinal distance between the vaginal orifice 36 and the posterior labial commissure 26. In addition, the length of the labia majora and minora may both vary significantly. For example, the longitudinal distance between the clitoris 40 and the urethral orifice 38 may range from about 0.5 to about 4 cm, while the longitudinal distance between the vaginal orifice 36 and the posterior labial commissure 26 may range from about 1 to about 5 cm. In addition to the variation in the previously described longitudinal distances, the longitudinal distance between the urethral 38 and vaginal 36 orifices can range from about 0.5 to about 4.5 cm.

With such variations in distances, the absorbent article 20 of the present invention allows the wearer to position the end region 50 having the maximum width ($W_{max}$) of the absorbent structure 46 adjacent the desired orifice to intercept the intended bodily exudate(s). For example, if the intended bodily exudate is menstrual fluid and the vaginal orifice 36 is located closer to the posterior labial commissure 26, the wearer may position the end region 50 having the maximum width ($W_{max}$) of the absorbent structure 46 under the vaginal orifice and thus closer to the posterior labial commissure. Alternatively, if the intended bodily exudate is menstrual fluid and the vaginal orifice 36 is located closer to the clitoris 40, the wearer may position the end region 50 having the maximum width ($W_{max}$) of the absorbent structure 46 under the vaginal orifice and thus closer to the clitoris. Still alternatively, if the intended bodily exudate is menstrual fluid and the vaginal orifice 36 is instead located at the midpoint between the clitoris 40 and the posterior labial commissure 26, the wearer may select and position an absorbent article 20 having an appropriate maximum width geometry under the vaginal orifice with the minimum width region of the absorbent being oriented closer to either the clitoris or the posterior labial commissure, whichever is most comfortable for the female wearer.

Consequently, the absorbent article 20 of the present invention may be reversibly oriented and selectively disposed with the minimum absorbent width ($W_{min}$) closest to the clitoris 40 or closest to the posterior labial commissure 26 in the vestibule 22 of a female wearer. Such reversibility allows for a female wearer to maximize comfort and conformability by placement of the absorbent article 20 within her vestibule in an orientation which results in a customized fit best suited to the location of her principal urogenital members and catamenial needs. By allowing such individualized placement, the female wearer is able to dispose the absorbent article 20 within her vestibule in an orientation where, in her opinion, (i) the most comfortable fit is obtained and (ii) she needs the maximum amount, i.e., maximum width ($W_{max}$), of the absorbent structure 46. Without desiring to be bound by theory, it is believed that the likelihood of leakage is minimized by affording a female wearer the opportunity to position the absorbent article 20 within her vestibule in an orientation that places the maximum width ($W_{max}$) of the absorbent 46 in close proximity to the chosen orifice to adsorb and/or absorb the desired exudate(s).

When folded along the axis of flexure (F), the absorbent article 20 suitably has a profile in which the highest point along the axis of flexure (as measured in the "Z" direction) is situated in the one of the longitudinal end regions 50, 52, rather than in the central region 54. As illustrated in FIG. 7, when so folded, the absorbent article 20 will form a recess 72 which protects the wearer's finger(s) from soiling as the absorbent article is positioned within the vestibule 22. The wearer may, therefore, hold the folded absorbent article 20 at the side edges 60, 62 and begin disposition as seen in FIG. 7. The absorbent article 20 may then be positioned within the vestibule 22 by the wearer exerting a force with a finger or fingers positioned in the recess 72 formed by the folded absorbent article. Once inserted, the absorbent article 20 may have a tendency to unfold in an attempt to fill the vestibule 22 and thus the outer surface of the intake liner 42 (i.e., the inner surface of the absorbent article) is maintained in contact with the tissues (i.e. labia) of the vestibule.

Figure 5:
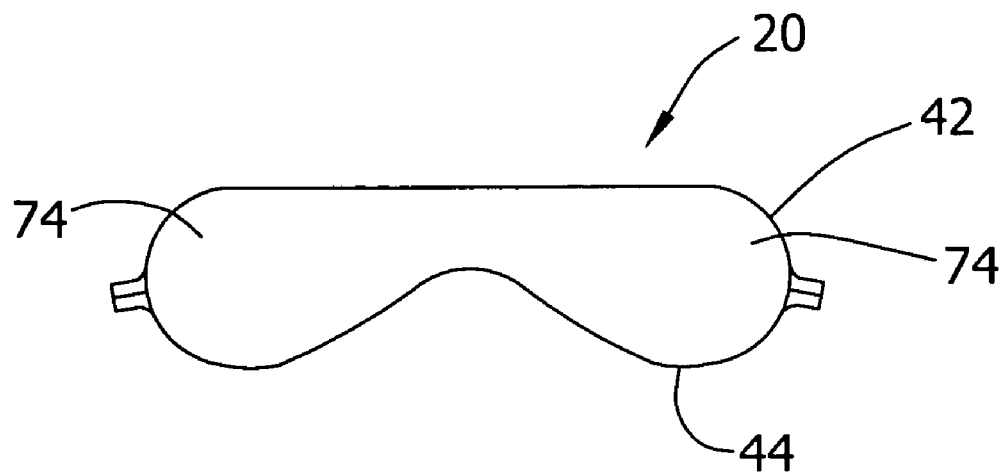
FIG. 5 is a cross-sectional view illustrating another embodiment of an absorbent article of the present invention.

The absorbent article 20 may be resiliently biased along the axis of flexure (F) to increase the tendency of the absorbent article to unfold. Alternatively, the absorbent structure 46 may be thicker (as at 74 in the illustrated embodiment of FIGS. 5 and 6) along its side edges 60, 62 to further provide an unfolding biasing effect intended to urge the liner 42 into contact with the tissues of the vestibule 22. An absorbent article 20, designed as described herein, does not necessarily require any additional features to maintain contact with the tissues of the vestibule 22 of the female wearer. The naturally moist surfaces of the tissues of the vestibule 22 typically demonstrate a tendency to maintain contact with the liner 42 of the absorbent article 20.

The bodyside liner 42 can alternatively have at least a portion of its outer surface treated with a suitable mucoadhesive to assist the absorbent article 20 in maintaining contact with the tissues of the vestibule 22 of the female wearer during use. These adhesives allow attachment of the absorbent article 20 to mucosal surfaces such as those of the inner labia. In use, the mucoadhesive suitably remains integrated with the absorbent article 20, which can still take in menstrual fluid through the liquid permeably liner 42. Suitable mucoadhesives include copolymers of polyethylene-polypropylene-polyethylene (PEO-PPO-PEO) tri-blocks with chitosan and polyacrylic acid. Another representative example is the hydrophobically modified bioadhesive produced from hydroxyethyl methacrylate, methyl methacrylate, and acrylic acid. Yet another representative example is a polyacrylic acid based synthetic polymer known as Carbopol and described in J. Controlled Release 39 93, 1996. Further information regarding mucoadhesives may be found in "Physico-Chemical Properties of Water Insoluble Polymers Important to Mucin/Epithelial Adhesion," H. Park and J. Robinson, J. Controlled Release, Vol. 2, (1985), pp. 47-57; and in "Development and Evaluation of a Mucoadhesive Drug Delivery System for Dual-Controlled Delivery of Nonoxynol-9," C. Lee and Y. Chien, J. Controlled Release, Vol. 39 (1996), pp. 91-103, both of which are incorporated herein by reference. Any suitable mucoadhesive familiar to one skilled in the art can be used.

Other configurations of the absorbent article are understood to be within the scope of this invention. For example, other suitable absorbent article configurations are disclosed in U.S. patent application Ser. Nos. 10/037,276 entitled "Labial Pad," filed Dec. 19, 2002, and 10/038,971 entitled "Absorbent Labial Pad," filed Dec. 12, 2002, each of which is incorporated herein by reference.

With respect to particular construction of the individual components of the absorbent article 20, the liner 42 is suitably constructed of a material that is flexible and non-irritating to the tissues within the vestibule 22 of a female wearer. As used herein, the term "flexible" is intended to refer to materials that are compliant and readily conform to the bodily surface(s), or that respond by easily deforming in the presence of external forces. The liner 42 suitably retains little or no liquid therein so that it provides a relatively comfortable surface next to the tissues within the vestibule 22. For example, the liner 42 may be constructed of any woven or nonwoven material that is easily penetrated by bodily liquids contacting its surface. Examples of suitable materials from which the liner 42 may be constructed include polypropylene or PP/PE or rayon; and those skilled in the art will recognize other useful materials such as polyethylene, nylon, or other heat-bondable fibers, polyolefins, such as copolymers of polypropylene and polyethylene, linear low-density polyethylene, aliphatic esters such as polyactic acid, and finely perforated film webs and net material also work well. One particularly suitable liner material is a bonded carded web made of polypropylene and polyethylene similar to the material used as a cover stock for KOTEX® pantiliners and obtainable from Sandler Corporation of Germany.

Other examples of suitable liner materials include composite materials of a polymer and a nonwoven fabric material. The composite materials are typically in the form of integral sheets generally formed by the extrusion of a polymer onto a web of spunbond material. The liquid permeable liner 42 can also contain a plurality of apertures (not shown) intended to increase the rate at which bodily fluid(s) can penetrate the liner for flow to the absorbent structure 46. A physiologically hydrous liner material is also suitable for use in the present invention. As used herein, the term "physiologically hydrous" is intended to connote a liner material that maintains a suitably moist interface between the tissues of the vestibule 22 and the absorbent article 20 when disposed in that vestibular environment. The liner 42 can also have at least a portion of its outer surface treated with a surfactant to render the cover more hydrophilic, which permits liquid to more readily permeate the liner 42. The surfactant may also diminish the possibility that the liquid, such as menstrual fluid, will flow off the liner 42 rather than being absorbed by the absorbent structure 46. One suitable approach provides for the surfactant to be substantially evenly distributed across at least a portion of the outer surface of the liner 42.

The liner 42 may be, but is not necessarily, secured to the absorbent structure 46 by bonding all or a portion of the adjacent surfaces to one another. A variety of bonding methods known to those skilled in the art may be utilized including, but are not limited to, the application of adhesives in a variety of patterns between the two adjoining materials, entangling at least portions of the adjacent surface of the absorbent structure 46 and the liner 42, or fusing at least portions of the adjacent surfaces of the liner to the absorbent structure.

The outer cover 44 is suitably constructed of a liquid impermeable material, and more suitably a liquid impermeable but gas permeable material to permit the passage of air and moisture vapor out of the absorbent structure while blocking the passage of liquid. One example of a suitable outer cover material is a micro-embossed, polymeric film, such as polyethylene, polypropylene or polyester (PP/PE) or cellulose, having a thickness in the range of about 0.025 mm to about 0.13 mm. Bicomponent films can also be used, as well as woven and nonwoven fabrics that have been treated to render them liquid-impermeable. Other suitable materials include a closed-cell polyolefin foam or a closed-cell polyethylene foam.

The outer cover 44 may be, but is not necessarily, secured to the absorbent structure 46 by bonding all or a portion of the adjacent surfaces to one another. Bonding methods known to those of skill in the art include, but are not limited to, ultrasonics, thermal bonding, or the application of adhesives in a variety of patterns between the two adjoining surfaces as previously described.

As shown in FIG. 3, the liner 42 and the outer cover 44 are arranged in superposed relationship with each other and extend slightly outward beyond the absorbent structure 46. The liner 42 and outer cover 44 are suitably bonded together about the periphery of the absorbent structure along a seam 64. Bonding may be by any conventional technique such as gluing, crimping, hot-sealing or the like. Alternatively, it is understood that the liner 42 may wrap about the entire absorbent structure to fully encase the absorbent structure, whereby the outer cover 44 may be omitted, without departing from the scope of this invention.

The absorbent structure 46 of the absorbent article 20 is suitably a non-woven web comprising both hydrophilic fibers and superabsorbent material. Examples of suitable hydrophilic fibers include naturally occurring organic fibers composed of intrinsically wettable material, such as cellulosic fibers. Suitable sources of cellulosic fibers include: wood fibers, such as bleached kraft softwood or hardwood, high-yield wood fibers, and ChemiThermoMechanical Pulp fibers; bagasse fibers; milkweed fluff fibers; wheat straw; kenaf; hemp; pineapple leaf fibers; or peat moss. Other hydrophilic fibers, such as regenerated cellulose and curled chemically stiffened cellulose fibers may also be densified to form absorbent structures that can expand to a higher loft when wetted. Pulp fibers may also be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids.

Other examples of suitable hydrophilic fibers include synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material that has a suitable hydrophilic moiety and is not readily removable from the fiber, or by sheathing a nonwettable, hydrophobic fiber with a hydrophilic polymer during or after the formation of the fiber. For the purposes of the present invention, it is contemplated that selected blends of the various types of fibers mentioned above may also be employed.

As used herein, a superabsorbent material refers to a water-swellable, water-insoluble organic or inorganic material capable, under the most favorable conditions, of absorbing at least about 10 times its weight and, more suitably, at least about 30 times its weight in an aqueous solution containing 0.9 weight percent sodium chloride solution in water. Suitable superabsorbent materials include natural, biodegradable, synthetic and modified natural polymers and materials. In addition, the superabsorbent materials can be inorganic materials, such as silica gels, or organic compounds such as cross-linked polymers. The term "cross-linked" used in reference to the superabsorbent material refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces. Examples of synthetic superabsorbent polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly (vinyl pyrrolidone), poly(vinylmorpholinone), poly(vinyl alcohol), and mixtures and copolymers thereof.

The superabsorbent material used in making the absorbent structure is suitably in the form of discrete particles. Superabsorbent particles can be of any suitable shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of superabsorbent material may also be used in the absorbent structure. The superabsorbent materials may be in various length and cross-sectional dimensions and may also be in various degrees of neutralization.

In one embodiment, the superabsorbent material has certain liquid handling characteristics, including a gel stiffness index which is suitably at least about 0.5, and more suitably at least about 0.6. In some embodiments, the gel stiffness index is suitably at least about 0.9. The gel stiffness index of a superabsorbent material generally refers to the ability of the material to resist deformation under load and is particularly defined herein as the absorbency under load value (AUL) of the superabsorbent material as determined by an Absorbency Under Load Test conducted at a load of about 0.9 psi, divided by the centrifuge retention capacity (CRC) of the superabsorbent material as determined by a Centrifuge Retention Capacity Test. The Absorbency Under Load Test and the Centrifuge Retention Capacity Test are set forth later herein.

As an example, one suitable superabsorbent material is made by Stockhausen, Inc. of Greensboro, N.C., U.S.A., under the designation FAVOR 9543. This superabsorbent material has an AUL at 0.9 psi (6.2 kPa) as determined by the AUL Test of about 21.6 g/g and a CRC as determined by the CRC Test of about 23.2 g/g. The gel stiffness index of such a superabsorbent material is therefore about 0.93. FAVOR 880, another suitable superabsorbent material made by Stockhausen, Inc., has an AUL at 0.9 psi (6.2 kPa) as determined by the AUL Test of about 21.3 g/g and a CRC as determined by the CRC Test of about 31.9 g/g. The FAVOR 880 therefore has a gel stiffness index of about 0.67.

The absorbency under load (AUL) value of the superabsorbent material is suitably at least about 12 grams/gram as determined by the AUL Test, and more suitably at least about 20 grams/gram.

The absorbent structure is suitably of unitary construction and may be formed in any conventional manner, such as by being air-formed, air-laid, bonded-carded or formed by other known techniques in which fibers and superabsorbent material are commingled to form a non-woven web. The superabsorbent material is suitably homogeneously mixed with the hydrophilic fibers to provide a uniform distribution of the superabsorbent material and fibers throughout the absorbent structure. Alternatively, the superabsorbent material may be distributed non-uniformly within the absorbent structure, such as across the width, along the length and/or through the thickness of the structure to define discrete target regions or zones of the structure within which the superabsorbent material is located. In general, the concentration of superabsorbent material within the absorbent structure is suitably in the range of about five weight percent (e.g., by weight) to about thirty-five weight percent of the weight of the absorbent structure 46, more suitably in the range of about fifteen weight percent to about thirty-five weight percent of the weight of the absorbent structure, and even more suitably in the range of about fifteen weight percent to about twenty-five weight percent of the weight of the absorbent structure.

It is also contemplated that the absorbent structure may be a multi-layered structure wherein the multiple layers may be of the same construction or they may have different properties, such as different basis weights, different densities, different materials, different superabsorbent concentrations, and the like without departing from the scope of this invention.

The absorbent structure 46 may or may not be wrapped or otherwise encompassed by a suitable tissue wrap for maintaining the integrity and/or shape of the absorbent structure during use.

The absorbent structure 46 suitably has a basis weight in the range of about 150 grams per square meter (gsm) to about 400 gsm. The density of the absorbent structure 46 is suitably in the range of about 0.05 grams per cubic centimeter (g/cc) to about 0.13 g/cc, and more suitably in the range of about 0.08 g/cc to about 0.13 g/cc.

A principal aspect of the invention pertains to features of the absorbent structure 46 and particularly improvements in the types, combinations and percentages of at least two fluid absorbing materials to achieve optimum results in the fluid intake and rewet performance and in the saturation and fluid retention capacity in absorbing bodily exudates, i.e., menses. In the past most absorbent materials could deliver either a good fluid intake rate or provide for an acceptable fluid capacity, but not both. Typical prior absorbents (with blends of cotton/rayon), selected as "control" absorbents for test purposes described later herein, show fast intake but relatively poor fluid retention. The superabsorbent material of the absorbent structure 46 described herein provides increased saturation and retention capacity to the absorbent structure so that the article incorporating the absorbent structure can be relatively small, thereby reducing the wearer's risk of embarrassment and providing the wearer with an opportunity to wear the article without feeling concerned about the size, comfort or visibility to others.

The absorbent structure 46 of the present invention suitably has certain liquid intake performance characteristics, including suitable liquid intake and rewet performance characteristics, a suitable saturation capacity and a suitable retention capacity, all of which are measurable using the tests described below. Intake performance refers generally to the ability of the absorbent structure to rapidly accept liquid therein. A fast intake time corresponds with a desirably low residence time of liquid on the outer surface of the absorbent article. Rewet performance refers to the ability of the absorbent structure to inhibit previously taken-in liquid against flowing back out of the absorbent structure when a compressive load is applied thereto, such as during normal activity including walking, sitting, twisting, bending, etc. A lower rewet amount corresponds to reduced surface wetness, which can improve wearer comfort and helps promote skin health. The saturation capacity of the absorbent structure is generally the maximum amount of liquid that the absorbent structure can retain, while the retention capacity refers to the ability of the absorbent structure to retain liquid when subjected to a compressive load such as that experienced during normal use.

As an example, in accordance with one embodiment of the present invention the absorbent structure 46 suitably has a saturation capacity as determined by the Saturation Capacity and Retention Capacity Test of at least about 15 grams/gram, and more suitably in the range of about 15 grams/gram to about 30 grams/gram. The retention capacity of the absorbent structure as determined by the Saturation Capacity and Retention Capacity Test is suitably at least about 3 grams/gram, and more suitably at least about 4 grams/gram. The intake time for a first insult of about 2 ml of menses simulant as determined by the Intake and Rewet Test set forth herein is suitably less than or equal to about thirty seconds. The rewet of the absorbent structure 46 as determined by the Intake and Rewet Test is suitably less than or equal to about 1.0 grams, and more suitably less than or equal to about 0.7 grams.

The absorbent structure 46 also has a suitable total absorbent capacity, which is a function of the size (e.g., length and width) of the absorbent structure, the basis weight of the absorbent structure, and the saturation capacity of the absorbent structure as determined by the Saturation Capacity and Retention Capacity Test. For example, the total absorbent capacity may be determined by multiplying the length (meters) of the absorbent structure 46 by the width (meters) thereof, then multiplying by the basis weight (grams per square meter), and then further multiplying by the saturation capacity (grams/gram) of the absorbent structure. As an example, the absorbent structure 46 suitably has a total absorbent capacity in the range of about grams to about 85 grams, and more suitably in the range of about 5 grams to about 40 grams.

The relatively small size of the absorbent structure 46 allows at least a portion of the absorbent structure (and hence the absorbent article containing the absorbent structure) to be disposed within the vestibule of the female wearer. For example, at least about 30 percent to 100 percent of the absorbent structure is suitably disposed within the vestibule during use, and more suitably about 50 percent of the absorbent structure is disposed within the vestibule during use.

Test Methods

Saturation Capacity and Retention Capacity Test

The Saturation Capacity aspect of the Test measures the amount of menses simulant that can be taken into and retained by an absorbent structure after being saturated and subjected to a slight compressive load under controlled conditions (e.g., to remove pooling from the surface of the absorbent structure). The Retention Capacity aspect of the Test measures the ability of the absorbent structure to retain menses simulant therein after being saturated and subjected to centrifugation under controlled conditions. The resultant saturation and retention capacities are each stated as gram weight of menses simulant retained per gram weight of the sample (g/g) tested. It is assumed for purposes of testing that one milliliter of menses simulant weighs one gram.

For the purposes of this Saturation Capacity and Retention Capacity Test, the menses simulant comprises a stock swine blood (having a Hematocrit value of about 40 to about 50 percent) mixed with plasma (having a Hematocrit value of zero percent) in a ratio which results in the menses simulant having a Hematocrit value of about 35 percent. Suitable techniques for determining the Hematocrit value of blood are well known in the art, as are suitable techniques for mixing the blood and plasma. Suitable stock swine blood and plasma is available from Cocalico Biologicals, Inc. of Reamstown, Pa., U.S.A.

Established guidelines for handling blood-borne pathogens, including personal protection, handling and post-use sterilization must be followed when working with the menses simulant. Prior to using the menses simulant for any procedure, the simulant is removed from the refrigerator and placed in a water bath for 10 minutes at 26° C. Before cutting open the bag for use, the bag is massaged between hands for a few minutes to mix the simulant, which will have separated in the bag. The bag tubing is then cut and the amount of simulant needed is poured out and stirred slowly to mix thoroughly before use.

Four samples of each absorbent structure to be tested are prepared, each having a size of approximately 1.5 inches (38.1 mm) square, and the results of the testing are averaged to determine the saturation capacity and retention capacity of the sample. Each sample to be tested is weighed and the dry weight of the sample is recorded before testing of the sample is conducted.

The Saturation Capacity part of the Test is conducted as follows. Approximately thirty milliliters (ml) of the menses simulant (at room temperature) is placed in a plastic dish. The sample to be tested is placed on a strip of plastic scrim (for handling purposes) and the scrim and sample are together placed in the plastic dish of menses simulant, making sure that the simulant completely covers the sample. The dish is then suitably covered to inhibit evaporation of the menses simulant. The sample is allowed to soak in the menses simulant under "free swell" conditions (e.g. without a restraining load) for a period of thirty minutes, checking the sample intermittently to make sure that excess simulant remains in the dish throughout the soaking period.

A piece of surge material sized approximately two inches (50.8 mm) square is placed on top of a stack of three pieces of blotter paper. The surge material is a through bonded carded web comprising 40 percent, 6 denier polyester fibers available from KOSA of Charlotte, N.C., U.S.A. and 60 percent, 3 denier bicomponent fibers (polyethylene-polypropylene sheath-core), available from ESFIBERVISION of Athens, Ga., U.S.A., at a basis weight of about 2.5 ounces per square yard (osy). A second piece of surge material (of same size and construction as the first piece) and a stack of two additional pieces of blotter paper are prepared but not used yet.

After the thirty minute soaking period, the sample is removed from the menses simulant using the scrim and the sample is flipped over (e.g., off of the scrim) onto the surge material resting on the stack of three pieces of blotter paper. The second piece of surge material is then placed over the sample and the stack of two additional pieces of blotter paper is placed over the second piece of surge material. A 0.05 pounds per square inch (psi) weight (i.e., a 2.5 inch (63.5 mm) square plastic panel weighing about 51 grams) is placed on top of the stack of two additional pieces of blotter paper to gently compress the soaked sample for a period of about five minutes. The weight, upper (second) pieces of blotter paper and upper (second) surge material are removed and the absorbent sample is transferred (using a pair of spatulas) onto a mesh screen of a conventional centrifuge testing apparatus (not shown) as described below. The weight of the mesh screen should be weighed prior to the first absorbent sample being placed thereon.

The wet sample and screen are then weighed together. To determine the saturation capacity of the sample, the dry sample and mesh screen weights are subtracted from the weight of the combined wet sample and screen, e.g., according to the following equation:

$$\text{Saturation Capacity} = \frac{\text{wet sample/screen weight} - \text{screen weight} - \text{dry sample weight}}{\text{dry sample weight}}$$

The Retention Capacity part of the Test is conducted on each sample subjected to the Saturation Capacity part. That is, after weighing the wet sample and screen to determine the saturation capacity of the sample, the wet sample and screen are together placed into a suitable centrifuge capable of subjecting the samples to a g-force of about 300 g. One suitable centrifuge is available from Kendro Laboratory Products of Newtown, Conn., U.S.A., under the designation SORVALL RT-6000D. Where multiple samples are centrifuged, the samples must be placed in opposing positions within the centrifuge to balance the screen when spinning. The samples are centrifuged at about 1,200 rpm (e.g., to achieve a target g-force of about 300 g), for 3 minutes. The sample and screen is removed and weighed. The amount of menses simulant retained by the sample is the retention capacity of the sample, expressed as grams of simulant per gram of sample. More particularly, the retention capacity is determined as:

$$\text{Retention Capacity} = \frac{\text{sample/screen weight after centrifuge} - \text{screen weight} - \text{dry sample weight}}{\text{dry sample weight}}$$

Intake and Rewet Test

The Intake and Rewet Test determines differences between absorbent structures designed for absorption of menses in the rate of intake and the amount of flow back to the surface (e.g., rewet) of the absorbent structure under pressure. A 4 inch by 4 inch (10.16 cm by 10.16 cm) sample of the subject absorbent structure 46 is used to perform the Intake and Rewet Test.

For the purposes of this Intake and Rewet Test, the menses simulant is a commercial menses simulant available from Cocalico Biologicals, Inc. of Reamstown, Pa., U.S.A. having a Hematocrit value of about 30±2 percent. Established guidelines for handling blood-borne pathogens, including personal protection, handling and post-use sterilization must be followed when working with the swine blood based menses simulant. Prior to using the menses simulant for any procedure, the simulant is removed from the refrigerator and placed in a water bath for 10 minutes at 26° C. Before cutting open the bag for use, the bag is massaged between hands for a few minutes to mix the simulant, which will have separated in the bag. The bag tubing is then cut and the amount of simulant needed is poured out and stirred slowly to mix thoroughly before use.

Figure 8:
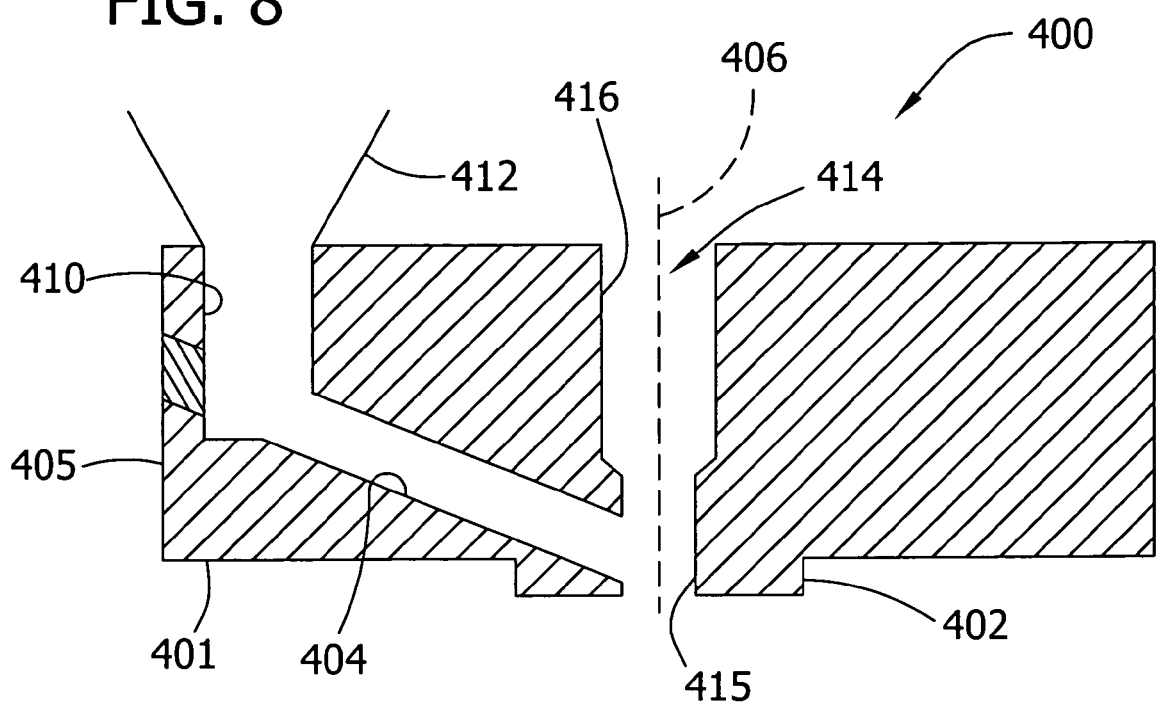
FIG. 8 is a vertical cross-section of a rate block for conducting an Intake and Rewet Test on absorbent structures.
Figure 9:
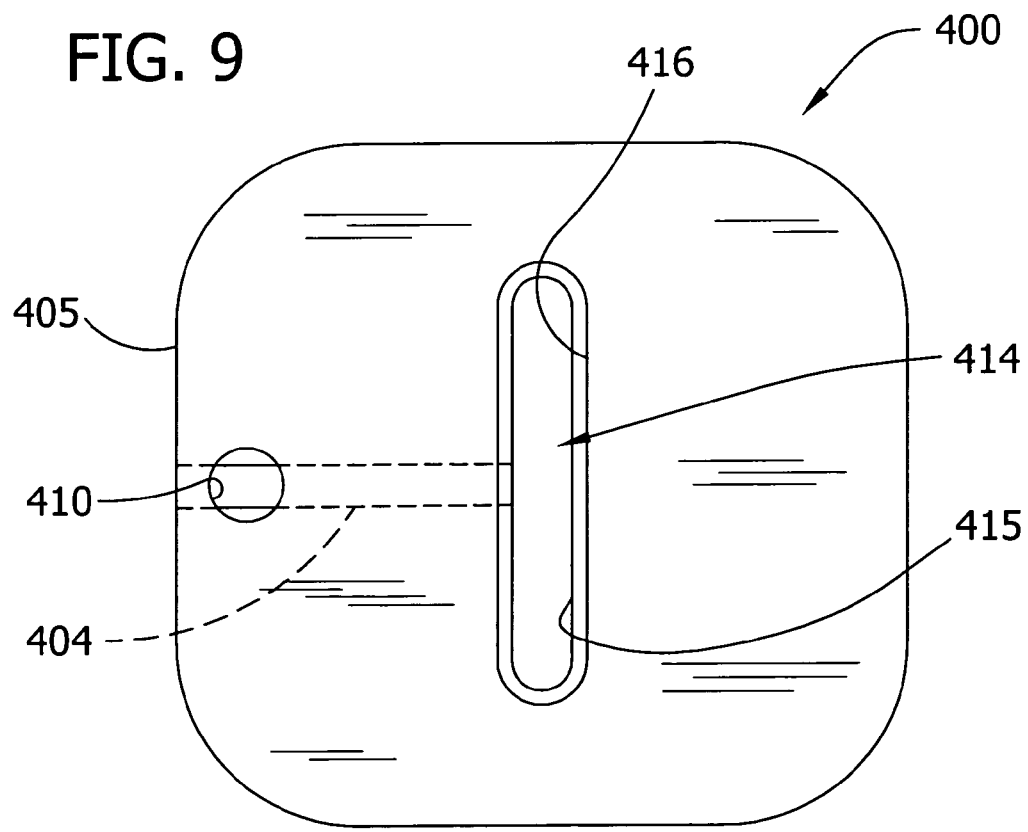
FIG. 9 is a plan view of the rate block of FIG. 8.

Referring to FIGS. 8 and 9, an acrylic rate block, generally indicated at 400, is 3 inches wide (76.2 mm) by 2.87 inches deep (72.9 mm) by 1.25 inches in height (31.8 mm). The rate block 400 includes a central portion 402 projecting out from the bottom 401 of the block, and a channel 404 extends diagonally downward from one side 405 of the rate block to a center line 406 thereof at an angle of about 22 degrees from horizontal. The channel 404 may be made by drilling the appropriately sized hole from the side 405 of the rate block 400 at the proper angle at a point above the bottom of the rate block; provided, however, that the starting point of the drill hole in the side 405 must be subsequently plugged so that menses simulant will not escape therefrom. A top hole 410 intersects the channel 404 and is on the side 405 and sized for receiving a funnel 412 therein. A central opening 414 allows viewing of the progression of the menses simulant as it is taken into the absorbent structure. The central slot 414 is centered width-wise on the rate block 400 and has a bottom hole outlet 415 that is smaller in size than at the top 416 of the rate block. The top hole 410 and central slot 414 may also be formed in the rate block 400 in any suitable manner. The rate block is sized to have a predetermined weight and thus exert a preselected pressure/area (i.e. a weight of 161.9 grams will exert a pressure of 0.62 kPa over an area of 25.6 cm².

Figure 10:
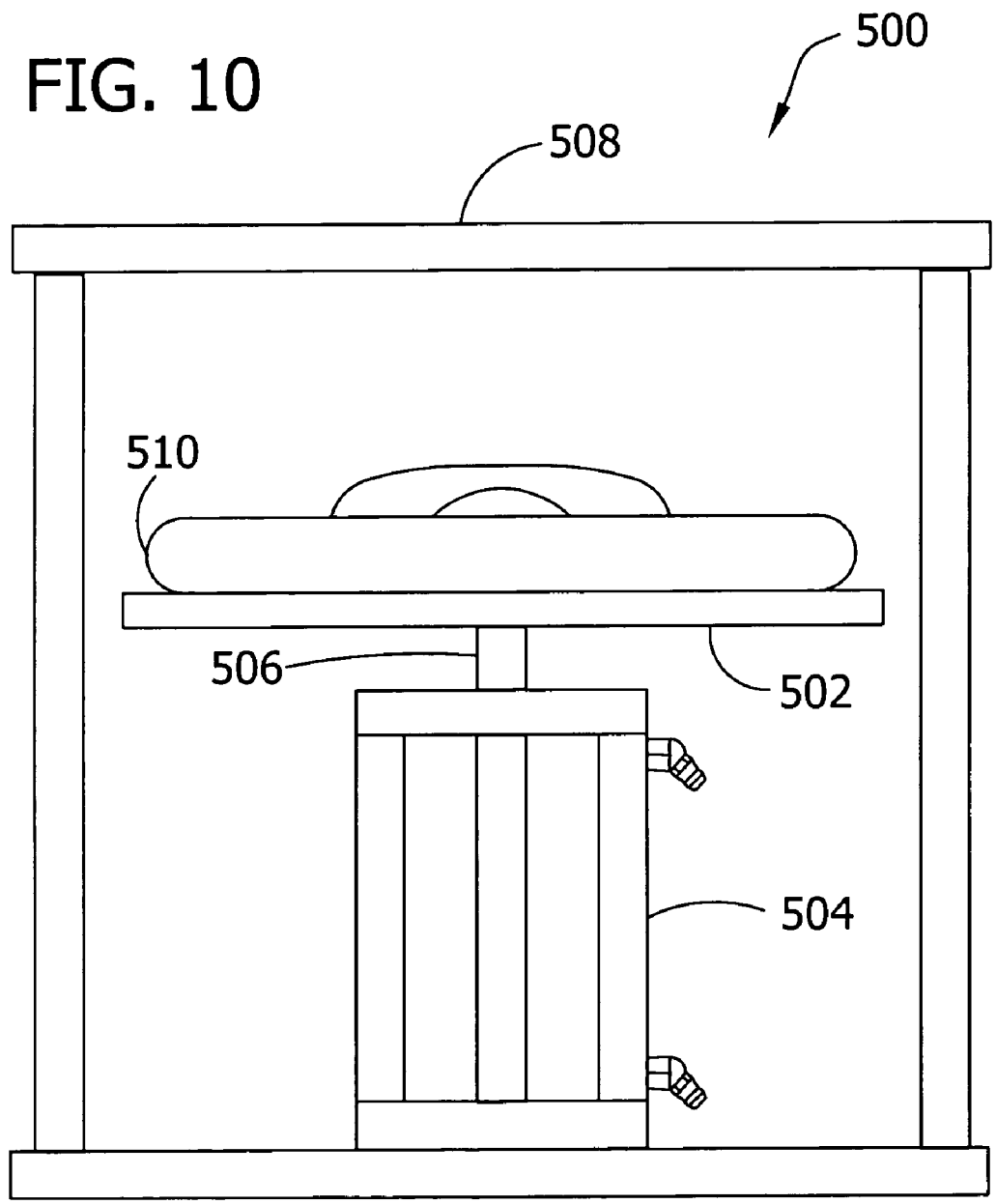
FIG. 10 is a side elevational view of a test stand for conducting the Intake and Rewet test.
Figure 11:
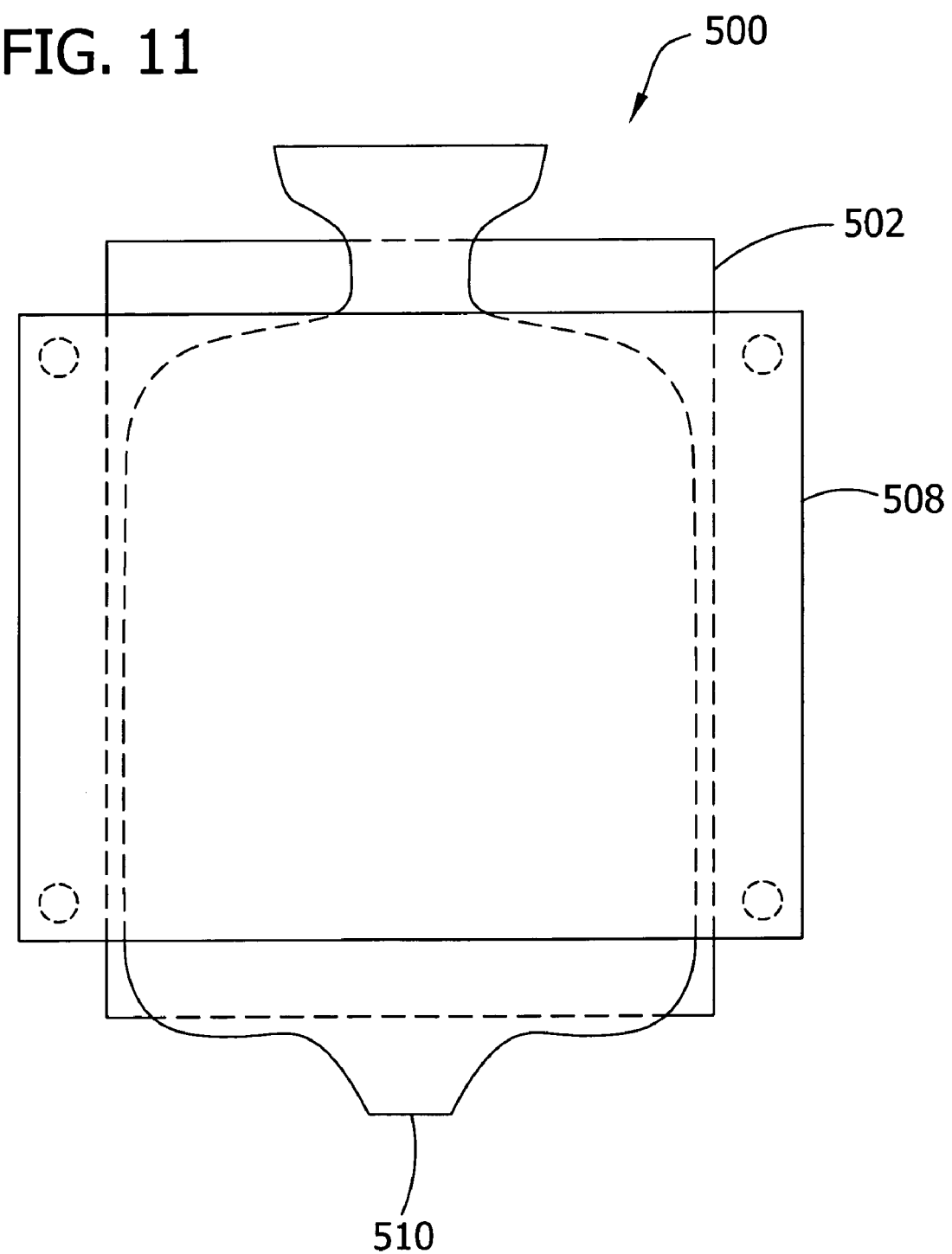
FIG. 11 is a plan view of the test stand of FIG. 10.

A test stand (shown in FIGS. 10 and 11 and indicated generally at 500) comprises a 7.75 inch by 10 inch (19.7 cm by 25.4 cm) platen 502 supported by a pneumatic cylinder 504 and piston 506 below a fixed plate 508. A hot water bottle 510 (approximately 7.5 inches by about 10.75 inches) filled with water is seated on the platen 502 which supports the sample to be tested. The piston 506 is moveable via pneumatic pressure within the cylinder 504 to raise the platen 502 and the hot water bottle 510 and sample supported by the platen toward the fixed plate 508 to generally squeeze the sample between the hot water bottle and the fixed plate 508. The pressure within the cylinder 504 is regulated by a suitable pressure regulator (not shown). The hot water bottle 510 evenly distributes pressure across the test sample (which may or may not have the same height in the center than it does at its edges) and, thus, the hot water bottle 510 must be sufficiently filled to allow equal pressure redistribution thereacross.

In conducting the Intake and Rewet Test, two blotters (not shown) are weighed dry. The rate block 400 is aligned with the long direction of the central opening 414 aligned with what would be the longitudinal direction of the absorbent structure material. The rate block 400 is then placed in the center of the sample to be tested and the sample is insulted with 2.0±0.01 ml of the menses simulant poured into the funnel 412. A stopwatch is started when the first insult reaches the test material. Once the simulant is taken completely into the sample, the stopwatch is stopped and the time on the stopwatch is recorded (e.g., in seconds) as the intake time of the first insult. The stopwatch is then reset. A timer is also started when the stopwatch is stopped and, after ten minutes have elapsed on the timer, a second insult of 2.0±0.01 ml of menses simulant is applied to the sample. The stopwatch is started to track the time needed for the sample to take in the second insult and the time is recorded as the second intake time.

After timing the intake of the second insult, the timer is reset and started. After ten minutes have elapsed on the timer, the rate block 400 is removed from the sample and the two dry, pre-weighed blotters are placed on top of the sample. The blotters are centered over the center of the wetted area of the sample and the sample and blotters are together placed on the platen 502 under hot water bottle 510 in the test stand 500. A uniform 1.0 psi (6.9 kPa) pressure is applied to the blotter paper/absorbent structure system via the pneumatic cylinder 504 and piston 506 for a period of 180 seconds. The blotters are then removed and weighed. The amount of rewet, in grams weight, is the difference between the weight of the blotters when wet and when dry.

The Intake and Rewet Test is conducted on five absorbent structure samples and the results are averaged to obtain the intake time and rewet data for a particular absorbent structure.

Absorbency Under Load Test

Figure 15:
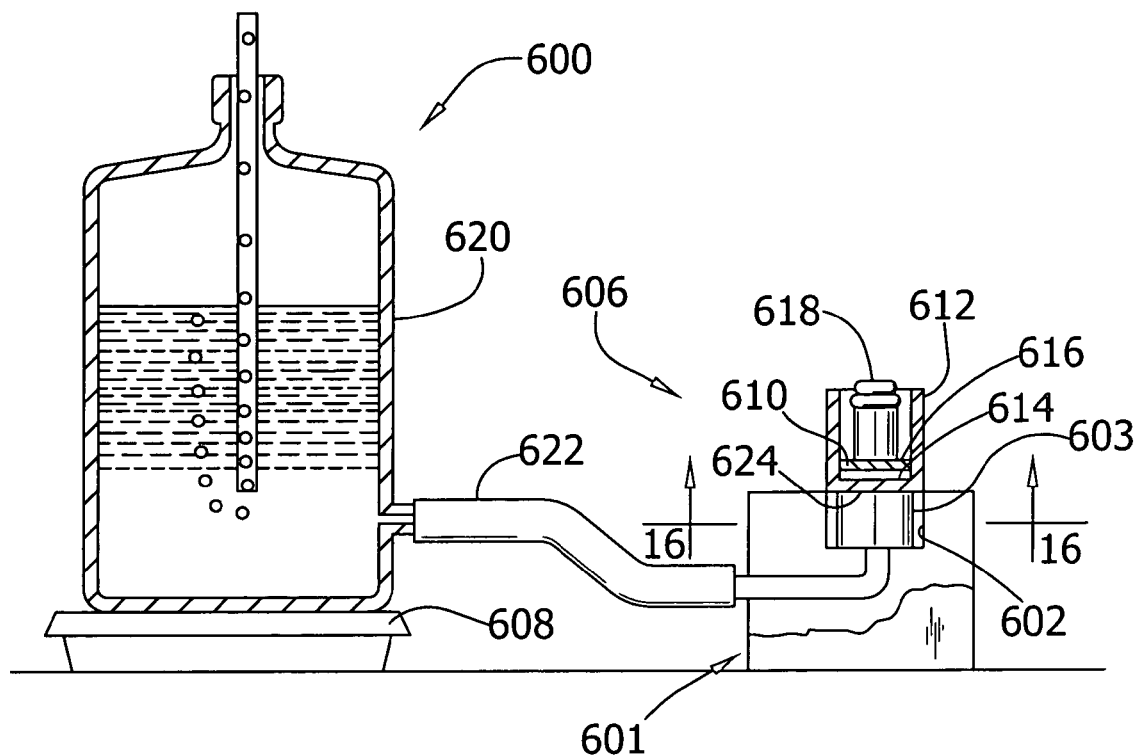
FIG. 15 is a cross-section of apparatus for conducting an Absorbency Under Load Test.

The Absorbency Under Load (AUL) Test measures the ability of a particulate absorbent gel material, e.g., such as a particulate superabsorbent material, to absorb a 0.9 weight percent solution of sodium chloride in distilled water at room temperature (test solution) while the material is under a 0.9 psi load. Apparatus 606 for conducting the AUL Test is shown in FIG. 15 and comprises a Demand Absorbency Tester (DAT), generally indicated at 600, which is similar to the Gravimetric Absorbency Test System (GATS) available from M/K Systems of Danners, Mass., U.S.A., and to the system described by Lichstein at pages 129-142 of the INDA Technological Symposium Proceedings, March 1974.

Figure 16:
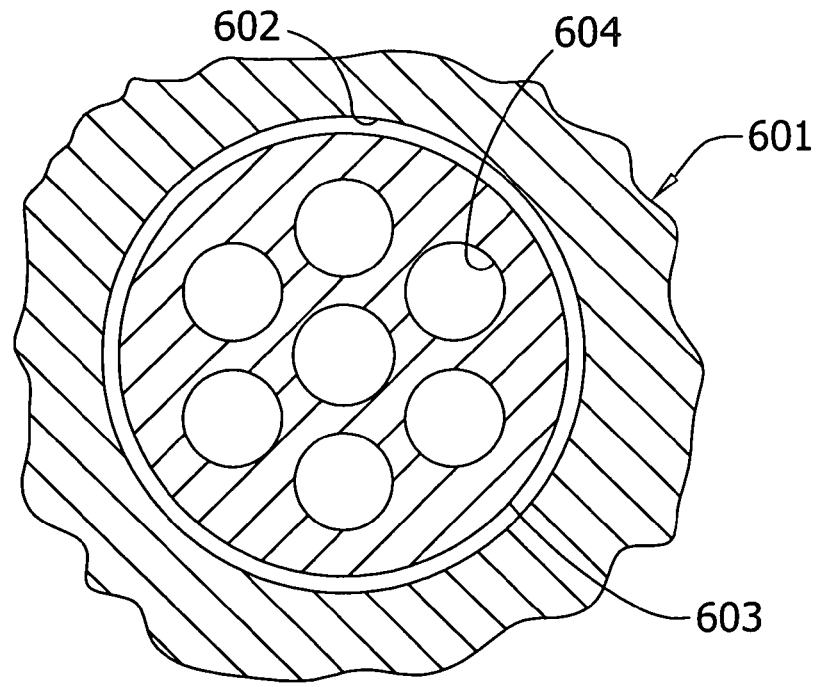
FIG. 16 is a section taken in the plane of line 16-16 of FIG. 15.

The test apparatus 606 further comprises a test stand, generally indicated at 601 (FIG. 16) having a cavity 602 formed therein and a porous plate 603 seated in the cavity and having a central porous area of about 2.54 cm diameter formed by a plurality of bores 604 extending through the plate. The cavity 602 shown in FIG. 16 has a diameter of about 3.2 cm and the porous plate 603 has a diameter of about 3.1 cm and comprises seven bores 604, each having a diameter of about 0.3 cm. One of the bores 604 is centrally located and the remaining six bores are concentrically positioned about the central bore with the spacing from the center of the central bore to the center of each adjacent bore is about one centimeter.

A sample container for containing a sample 610 to be tested comprises a cylinder 612 and a stainless steel cloth screen 614 that is biaxially stretched to tautness and attached to the lower end of the cylinder. The cylinder 612 may be bored from a transparent LEXAN rod or equivalent material, or it may be cut from a LEXAN tubing or equivalent material, and has an inner diameter of about one inch (about 2.54 cm). The stainless steel cloth screen 614 is suitably a 100 mesh screen A disc, or piston 616 is machined from a LEXAN rod, Plexiglass or equivalent material and has a diameter sized such that it fits within the cylinder 612 with minimum wall clearance but still slides freely. The height of the piston 616 is approximately 0.8 cm and the weight of the piston is suitably about 4.4 grams to provide a load over the cross-sectional area of the sample in the container of about 0.01 psi. A weight 618 is sized (e.g., having a diameter of about 2.5 cm) for seating on the piston 616 to increase the load (e.g., in addition to the weight of the piston) on the sample. For example, a weight of about 317 grams is used to provide a load (e.g., including the piston weight) of about 0.9 psi over the cross-sectional area of the sample in the container.

The cavity 602, and hence the porous plate 603, is in fluid communication with a reservoir 620 containing test solution (0.9 weight percent sodium chloride solution in distilled water at room temperature) via a suitable conduit 622. As shown in FIG. 15, the reservoir 620 is seated on an electrostatic balance 608.

A sample 610 of particulate superabsorbent material weighing about 0.160 grams is prepared by screening the particles through a U.S. standard 30 mesh screen and retaining the particles on a U.S. standard 50 mesh screen so that the sample comprises particles in the size range of about 300 to about 600 microns. The sample is weighed on suitable weighing paper and then loaded into the sample container (with the piston 616 removed) so that the particles are uniformly distributed and uniformly distributed and overlay the screen at the bottom of the container. The sample container is gently tapped to level the bed of particles in the container.

The AUL Test is initiated by placing a circular piece of GF/A glass filter paper 624 onto the porous plate 603 over the bores 604 formed therein and allowing to become saturated by test solution delivered from the reservoir 620 to the porous plate via the conduit 622. The paper 624 is suitably sized larger than the inner diameter of the cylinder 612 and smaller than the outer diameter thereof to ensure good contact while inhibiting evaporation over the bores 604. The electrostatic balance 608 is zeroed at this time. The piston 616 and weight 618 are placed on the sample within the container and the container (with the sample, piston and weight therein) is placed on the plate 603 over the saturated glass filter paper 624 to allow test solution to be taken into the sample in the container via the conduit 622, bores 604 in the plate 602 and the filter paper.

The electrostatic balance 608 is used to measure the flow of test solution to the sample over a period of about 60 minutes. The amount (in grams) of solution taken into the sample after about 60 minutes divided by the dry weight of the sample (e.g., about 0.160 grams) is the AUL value of the sample in grams of liquid per gram weight of sample.

Two checks can be made to ensure the accuracy of the measurement. First, the height the piston 616 rises above the screen 614 at the bottom of the sample container multiplied by the cross-sectional area of the piston should roughly equal the amount of solution picked up by the sample over the 60 minute period. Second, the sample container can be weighed before (e.g., while the superabsorbent material is dry) and after the test and the difference in weight should roughly equal the amount of solution picked up by the sample over the 60 minute period.

A minimum of three tests is performed and the results are averaged to determine the AUL value at 0.9 psi. The samples are tested at 23±1 degrees Celsius at 50±2 percent relative humidity.

Centrifuge Retention Capacity Test

The Centrifuge Retention Capacity (CRC) Test measures the ability of the superabsorbent material particles to retain liquid therein after being saturated and subjected to centrifugation under controlled conditions. The resultant retention capacity is stated as grams of liquid retained per gram weight of the sample (g/g). The sample to be tested is prepared from particles which are prescreened through a U.S. standard 30 mesh screen and retained on a U.S. standard 50 mesh screen. As a result, the sample comprises particles sized in the range of about 300 to about 600 microns. The particles can be prescreened by hand or automatically and are stored in a sealed airtight container until testing.

The retention capacity is measured by placing 0.2±0.005 grams of the prescreened sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is placed in the pouch, the remaining open edge of the pouch is also heat-sealed. Empty bags are also made to serve as controls. Three samples (e.g., filled and sealed bags) are prepared for the test. The filled bags must be tested within three minutes of preparation unless immediately placed in a sealed container, in which case the filled bags must be tested within thirty minutes of preparation.

The bags are placed between two TEFLON® coated fiberglass screens having 3 inch openings (Taconic Plastics, Inc., Petersburg, N.Y.) and submerged in a pan of the test solution at 23 degrees Celsius, making sure that the screens are held down until the bags are completely wetted. After wetting, the samples remain in the solution for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the retention capacity is determined as:

$$CRC = \frac{\text{sample/bag weight after centrifuge} - \text{empty bag weight after centrifuge} - \text{dry sample weight}}{\text{dry sample weight}}$$

The three samples are tested and the results are averaged to determine the centrifuge retention capacity (CRC). The samples are tested at 23±1 degrees Celsius at 50±2 percent relative humidity.

Experiment

Absorbent structure samples having different materials of construction, basis weight and density were made in laboratory air-forming apparatus and subjected to the Saturation Capacity and Retention Capacity Test and the Intake and Rewet Test to evaluate the relationships between the various absorbent structure designs and the liquid performance characteristics for these absorbent structures in taking in menses simulant. The table in FIG. 12 identifies 12 different absorbent structure types which were tested. The first five codes in the FIG. 12 table identify comparative, or control absorbent structures formed from a mixture of rayon and cotton fibers (abbreviated as COT/RAY in the table) with the concentration of fibers varying for the different codes. For example, the absorbent structure of code 1 comprises 30 weight percent cotton fibers and 70 weight percent rayon fibers (indicated as 30/70 in the table). The basis weight and density of the absorbent structures of each of the first five codes also varied as indicated in the table.

The remaining codes (6-11) in the table of FIG. 12 identify absorbent structures comprised of a homogenous mixture of hydrophilic fibers and superabsorbent material. More particularly, the absorbent structure of code 6 comprises 15 weight percent superabsorbent material available from Stockhausen, Inc. of Greensboro, N.C., U.S.A. as FAVOR 880 (abbreviated as F880) and 85 weight percent of a mixture of cotton and rayon fibers. Codes 7-9 identify absorbent structures comprised of various concentrations of the FAVOR 880 superabsorbent material, ranging from 15 weight percent to 30 weight percent, mixed with wood pulp fibers available from Weyerhauser, Inc. of Tacoma, Wash., U.S.A. as CF416 and NB416 (the different designations representing generally the same wood pulp processed at two different mills).

The absorbent structures of codes 10 and 11 comprise a mixture of the CF416 or NB416 fibers and another superabsorbent material available from Stockhausen, Inc. as FAVOR 9543 (abbreviated as F9543). The FAVOR 9543 superabsorbent material is known as generally having a lower absorbent capacity than the FAVOR 880 superabsorbent material, but having a higher gel stiffness index. For example, the gel stiffness index of the FAVOR 880 superabsorbent material as determined by the Absorbency Under Load (AUL) Test and Centrifuge Retention Capacity (CRC) Test is about 0.67 and the gel stiffness index of the FAVOR 9543 as determined by the AUL Test and the CRC Test is about 0.93 g/g. The basis weight and density of each absorbent structure tested is also recorded in the table of FIG. 12.

Figure 13:
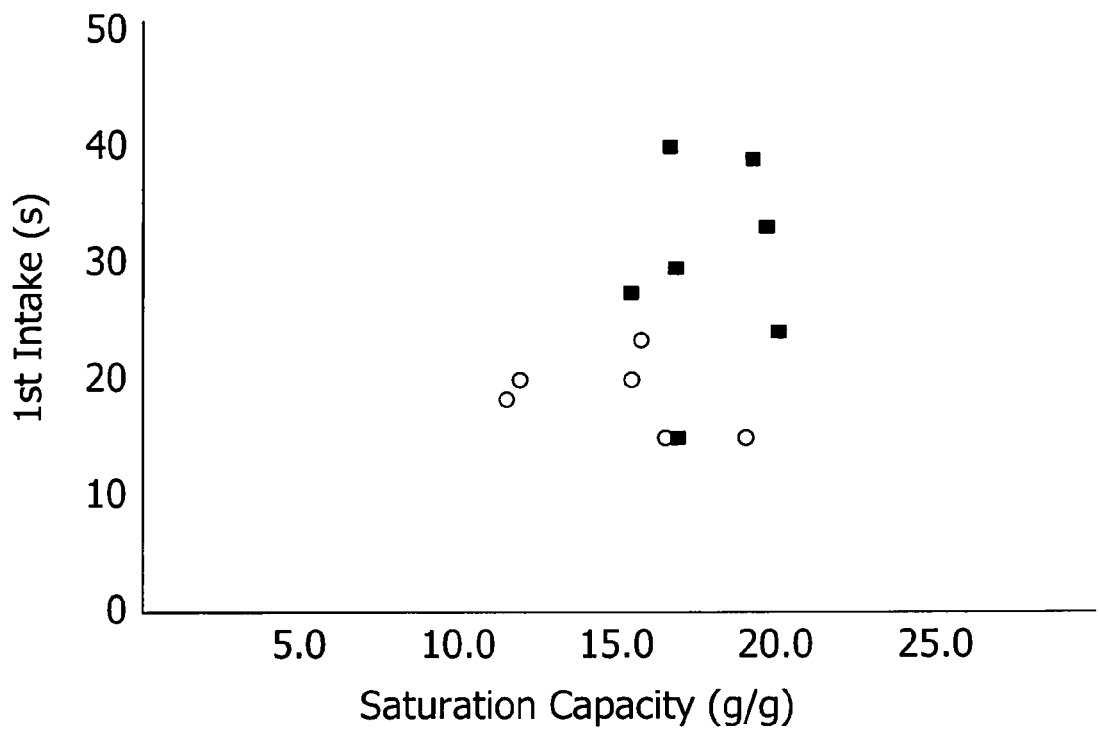
FIG. 13 is a plot of first intake rate versus intake saturation capacity of the absorbent structures set forth in the table of FIG. 12.
Figure 14:
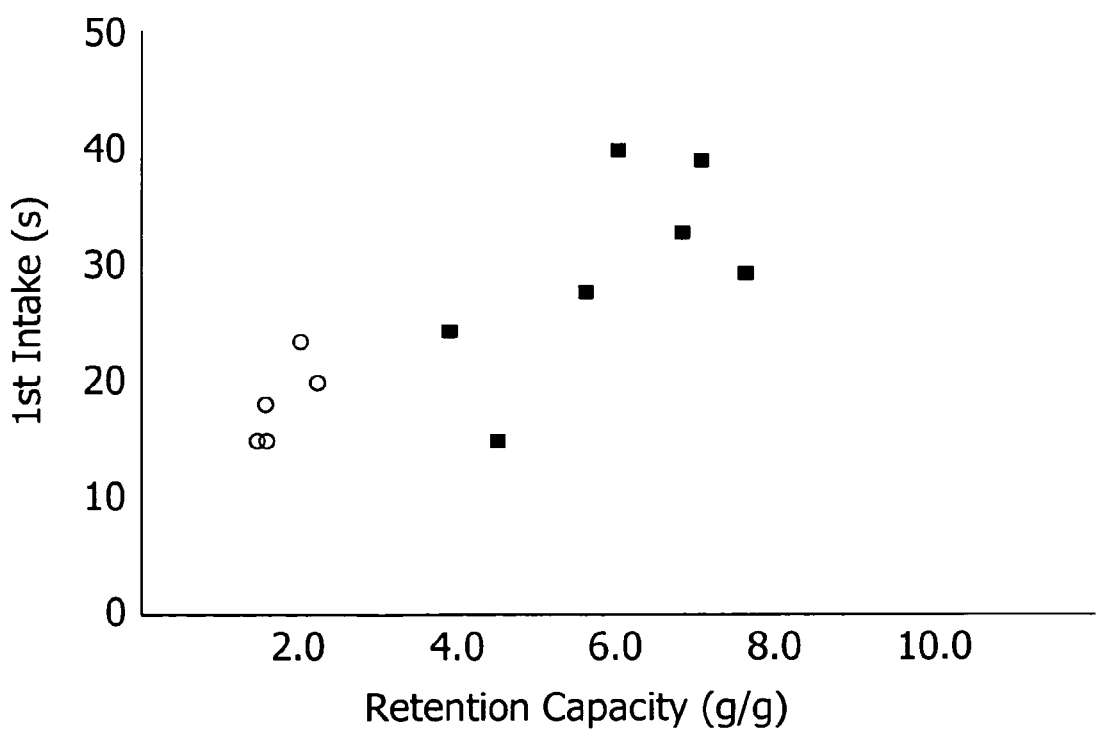
FIG. 14 is a plot of first intake rate versus retention capacity thereof.

The results of the Saturation Capacity and Retention Capacity Test and the Intake and Rewet Test are provided in the table of FIG. 12 as well as in the plots of FIGS. 13 and 14. More particularly, FIG. 13 graphically plots the first intake time (seconds) of each of the absorbent structures as measured by the Intake and Rewet Test against the saturation capacity (g/g) of the absorbent structures as determined by the Saturation Capacity and Retention Capacity Test; and FIG. 14 is a plot of the first intake time versus the retention capacity (g/g) of the respective absorbent structures. For comparison purposes in each of FIGS. 13 and 14, the five control absorbent structures are indicated with circles and the other absorbent structures are indicated with solid squares.

The test results of the group of control absorbent structures (items 1-5) show relatively good intake times, particularly for the first insult of menses simulant. However, these absorbent structures each have a low retention capacity (e.g., well below about 3 grams/gram) because the absorbent structures lack sufficient absorbent material to absorb and retain the menses simulant. In contrast, the retention capacity of each of the absorbent structures (codes 6-11) containing superabsorbent material is substantially greater (e.g., at least about 3 grams/gram) than that of the control absorbent structures. The rewet of the superabsorbent material containing absorbent structures is also improved relative to the control absorbent structures.

Among the absorbent structures containing superabsorbent material (codes 6-11), the density and superabsorbent material concentration of each absorbent structure also played a role in the liquid intake performance thereof. For example, the absorbent structures of codes 7, 9, 11 and 12 all had densities of at least 0.13 g/cc. The retention capacity of each of these absorbent structures was substantially greater than that of the control absorbent structures, as well as that of the other absorbent structures containing superabsorbent material. However, the first intake time for each of these absorbent structures was relatively high, i.e., 29 seconds for the absorbent structure of code 9 and greater than 30 seconds for the absorbent structures of codes 7 and 11.

FIG. 13 graphically depicts that the absorbent structures containing superabsorbent material (codes 6-11) each provide a saturation capacity of at least 15 grams/gram, which is generally greater than that of the control absorbent structures without superabsorbent material. The plot also shows that the use of superabsorbent material tends to increase the first intake time of the absorbent structure relative to the control absorbent structures. FIG. 14 also graphically depicts the absorbent structures containing superabsorbent material (codes 6-11) having substantially greater retention capacity than the control absorbent structures. More particularly, the retention capacity of the absorbent structures of codes 6-11 is at least 3 g/g and for the absorbent structures comprising absorbent fibers such as the pulp fluff (codes 7-11) the retention capacity is at least 4 g/g. Also, as indicated in the data table of FIG. 12, the absorbent structures of codes 7-11 (having superabsorbent material and pulp fluff) have a lower rewet than the other absorbent structures.

Thus, while the use of conventional mixes of cotton and rayon fibers or absorbent fibers (e.g., pulp fluff) are alone capable of achieving some of the performance characteristics of the present invention, by itself these materials are incapable of achieving all of the desired performance characteristics. The addition of superabsorbent material generally has the effect of increasing the retention capacity of the absorbent structure, but the addition of too much superabsorbent material can increase the intake time of the absorbent structure to undesirably high levels.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description shall be interpreted as illustrative and not in a limiting sense.

What is claimed is:

1. An absorbent article for disposition at least partially within the vestibule of a female wearer, said absorbent article comprising:
   a liquid permeable liner adapted for contiguous relationship with the wearer;
   an outer cover in generally superposed relationship with the liner; and
   an absorbent structure formed separate from the liner and the outer cover and being disposed therebetween, said absorbent structure being sized and configured for insertion at least partially within the vestibule of the female wearer, said absorbent structure being constructed at least in part of hydrophilic fibers and superabsorbent material, a concentration of the superabsorbent material in the absorbent structure being in the range of about 5 weight percent to about 35 weight percent, said superabsorbent material having a gel stiffness index of at least about 0.5, said absorbent structure having a saturation capacity as determined by a Saturation Capacity and Retention Capacity Test of at least about 15 grams/gram, a retention capacity as determined by said Saturation Capacity and Retention Capacity Test of at least about 3 grams/gram, and an intake time for a first insult of said absorbent structure as determined by an Intake and Rewet Test of no more than about 30 seconds.

2. The absorbent article set forth in claim 1 wherein the absorbent structure comprises in the range of about 15 weight percent to about 35 weight percent superabsorbent material.

3. The absorbent article set forth in claim 2 wherein the absorbent structure comprises in the range of about 15 weight percent to about 25 weight percent superabsorbent material.

4. The absorbent article set forth in claim 1 wherein the superabsorbent material has a gel stiffness index of at least about 0.6.

5. The absorbent article set forth in claim 1 wherein the retention capacity of the absorbent structure as determined by the Saturation Capacity and Retention Capacity Test is at least about 4 grams/gram.

6. The absorbent article set forth in claim 1 wherein the absorbent structure has a density in the range of about 0.05 grams/cubic centimeters to about 0.13 grams/cubic centimeters.

7. The absorbent article set forth in claim 6 wherein the absorbent structure has a density in the range of about 0.08 grams/cubic centimeters to about 0.13 grams/cubic centimeters.

8. The absorbent article set forth in claim 7 wherein the absorbent structure has a density in the range of about 0.08 grams/cubic centimeters to about 0.11 grams/cubic centimeters.

9. The absorbent article set forth in claim 1 wherein absorbent structure has a maximum length in the range of about 60 to about 100 millimeters and a maximum width in the range of about 40 to about 70 millimeters.

10. The absorbent article set forth in claim 1 wherein the absorbent structure has a thickness in the range of about 1 to about 8 millimeters.

11. The absorbent article set forth in claim 10 wherein the absorbent structure has a thickness in the range of about 1 to about 5 millimeters.

12. The absorbent article set forth in claim 11 wherein the absorbent structure has a thickness in the range of about 2 to about 3 millimeters.

13. The absorbent article set forth in claim 1 wherein the absorbent structure has a basis weight in the range of about 150 to about 400 grams per square meter.

14. The absorbent article set forth in claim 13 wherein the absorbent structure has a basis weight in the range of about 200 to about 350 grams per square meter.

15. The absorbent article set forth in claim 1 wherein the absorbent article has a predetermined axis of flexure extending generally longitudinally of said article, the absorbent structure being foldable on said predetermined axis of flexure.

16. The absorbent article set forth in claim 1 wherein the absorbent structure comprises a mixture of superabsorbent material and hydrophilic fibers.

17. The absorbent article set forth in claim 16 wherein the mixture of superabsorbent material and hydrophilic fibers is a generally homogeneous mixture.

18. The absorbent article set forth in claim 1 wherein the absorbent structure is of unitary construction.

19. The absorbent article set forth in claim 1 wherein the absorbent structure further has a rewet as determined by the Intake and Rewet Test of less than or equal to about 1 gram.

20. The absorbent article set forth in claim 19 wherein the absorbent structure has a rewet as determined by the Intake and Rewet Test of less than or equal to about 0.7 grams.

21. The absorbent article set forth in claim 1 wherein the absorbent structure has a saturation capacity as determined by a Saturation Capacity and Retention Capacity Test in the range of about 15 grams/gram to about 30 grams/gram.

22. The absorbent article set forth in claim 1 wherein the absorbent structure has a retention capacity as determined by a Saturation Capacity and Retention Capacity Test in the range of about 3.9 grams/gram to about 7.6 grams/gram.

23. The absorbent article set forth in claim 1 wherein the absorbent structure has an intake time for a first insult of said absorbent structure as determined by an Intake and Rewet Test of greater than or equal to about 15 seconds.

24. The absorbent article set forth in claim 1 wherein the absorbent structure has a saturation capacity as determined by a Saturation Capacity and Retention Capacity Test in the range of about 15 grams/gram to about 30 grams/gram, a retention capacity as determined by a Saturation Capacity and Retention Capacity Test in the range of about 3.9 grams/gram to about 7.6 grams/gram, and an intake time for a first insult of said absorbent structure as determined by an Intake and Rewet Test of greater than or equal to about 15 seconds.

25. An absorbent article for disposition at least partially within the vestibule of a female wearer, said absorbent article comprising:
an absorbent structure sized and configured for insertion at least partially within the vestibule of the female wearer, said absorbent structure comprising in the range of about 5 weight percent to about 15 weight percent superabsorbent material, said absorbent structure having a basis weight in the range of about 150 to about 400 grams per square meter and a density in the range of about 0.05 to about 0.13 grams per cubic centimeter, said absorbent structure having a saturation capacity as determined by a Saturation Capacity and Retention Capacity Test of at least about 15 grams/gram and a retention capacity as determined by said Saturation Capacity and Retention Capacity Test of at least about 3 grams/gram.

26. The absorbent article set forth in claim 25 wherein the retention capacity of the absorbent structure as determined by the Saturation Capacity and Retention Capacity Test is at least about 4 grams/gram.

27. The absorbent article set forth in claim 25 wherein the absorbent structure has a density in the range of about 0.08 grams/cubic centimeters to about 0.13 grams/cubic centimeters.

28. The absorbent article set forth in claim 27 wherein the absorbent structure has a density in the range of about 0.08 grams/cubic centimeters to about 0.11 grams/cubic centimeters.

29. The absorbent article set forth in claim 25 wherein the absorbent structure has an intake time for a first insult of said absorbent structure as determined by an Intake and Rewet Test of no more than about 30 seconds.

30. The absorbent article set forth in claim 25 wherein absorbent structure has a maximum length in the range of about 60 to about 100 millimeters and a maximum width in the range of about 40 to about 70 millimeters.

31. The absorbent article set forth in claim 25 further comprising a liquid permeable liner adapted for contiguous relationship with the wearer, and an outer cover in generally superposed relationship with the liner, the absorbent structure being disposed between the liner and the outer cover.

32. The absorbent article set forth in claim 25 wherein the absorbent article has a predetermined axis of flexure extending generally longitudinally of said article, the absorbent structure being foldable on said predetermined axis of flexure.

33. The absorbent article set forth in claim 25 wherein the absorbent structure comprises a mixture of superabsorbent material and hydrophilic fibers.

34. The absorbent article set forth in claim 33 wherein the mixture of superabsorbent material and hydrophilic fibers is a generally homogeneous mixture.

35. The absorbent article set forth in claim 25 wherein the absorbent structure is of unitary construction.

36. The absorbent article set forth in claim 25 wherein the superabsorbent material has a gel stiffness index of at least about 0.5.

37. The absorbent article set forth in claim 36 wherein the superabsorbent material has a gel stiffness index of at least about 0.6.

38. The absorbent article set forth in claim 25 wherein the absorbent structure further has a rewet as determined by the Intake and Rewet Test of less than or equal to about 1 gram.

39. The absorbent article set forth in claim 38 wherein the absorbent structure has a rewet as determined by the Intake and Rewet Test of less than or equal to about 0.7 grams.

40. The absorbent article set forth in claim 25 wherein the absorbent structure has a saturation capacity as determined by a Saturation Capacity and Retention Capacity Test in the range of about 15 grams/gram to about 30 grams/gram.

41. The absorbent article set forth in claim 25 wherein the absorbent structure has a retention capacity as determined by a Saturation Capacity and Retention Capacity Test in the range of about 3.9 grams/gram to about 7.6 grams/gram.

42. The absorbent article set forth in claim 25 wherein the absorbent structure has a saturation capacity as determined by a Saturation Capacity and Retention Capacity Test in the range of about 15 grams/gram to about 30 grams/gram, and a retention capacity as determined by a Saturation Capacity and Retention Capacity Test in the range of about 3.9 grams/gram to about 7.6 grams/gram.

* * * * *